United States Patent
Hoang et al.

(10) Patent No.: US 9,750,922 B2
(45) Date of Patent: Sep. 5, 2017

(54) SYSTEMS AND METHODS FOR PROVIDING AN ANTIMICROBIAL DISPENSING APPLICATOR

(71) Applicant: Becton, Dickinson and Company, Franklin Lakes, NJ (US)

(72) Inventors: Minh Quang Hoang, Sandy, UT (US); Huibin Liu, West Jordan, UT (US); Jonathan Karl Burkholz, Salt Lake City, UT (US); Bryan G. Davis, Sandy, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 335 days.

(21) Appl. No.: 14/185,820

(22) Filed: Feb. 20, 2014

(65) Prior Publication Data
US 2015/0231380 A1    Aug. 20, 2015

(51) Int. Cl.
| | | |
|---|---|---|
| *A61F 13/40* | (2006.01) | |
| *B65B 3/00* | (2006.01) | |
| *B65B 7/14* | (2006.01) | |
| *B65B 51/10* | (2006.01) | |

(52) U.S. Cl.
CPC .......... *A61M 35/006* (2013.01); *B65B 3/003* (2013.01); *B65B 7/14* (2013.01); *B65B 51/10* (2013.01)

(58) Field of Classification Search
CPC ............................. A61M 35/006; A61F 13/38
USPC .......................................................... 604/3
See application file for complete search history.

(56) References Cited

U.S. PATENT DOCUMENTS

| | | | |
|---|---|---|---|
| 3,324,855 A | | 6/1967 | Heimlich |
| 3,757,782 A | | 9/1973 | Aiken |
| 3,774,609 A | | 11/1973 | Schwartzman |
| 4,173,978 A | | 11/1979 | Brown |
| 4,430,013 A | * | 2/1984 | Kaufman ............... A45D 34/04 401/132 |
| 4,747,719 A | | 5/1988 | Parkin |
| 4,799,815 A | | 1/1989 | Barabino et al. |
| 4,812,067 A | | 3/1989 | Brown et al. |
| 4,863,422 A | | 9/1989 | Stanley |
| 4,957,385 A | * | 9/1990 | Weinstein ........... A61M 35/006 206/530 |
| 5,035,348 A | | 7/1991 | Seifert |
| 5,100,028 A | | 3/1992 | Seifert |
| 5,120,301 A | | 6/1992 | Wu |
| 5,152,742 A | | 10/1992 | Simpson |
| 5,288,159 A | * | 2/1994 | Wirt .................... A61M 35/006 206/532 |

(Continued)

*Primary Examiner* — Susan Su
(74) *Attorney, Agent, or Firm* — Jeanne Lukasavage; Craig Metcalf; Kirton McConkie

(57) ABSTRACT

A handheld antiseptic dispensing applicator device having a reservoir for storing an antiseptic agent, the reservoir being coupled to an applicator pad, and a defeatable membrane or barrier being interposed between the reservoir and the applicator pad. Embodiments of the device comprise a squeezable reservoir, wherein the internal hydraulic pressure of the squeezable reservoir is increased via user applied forces to thereby defeat the membrane releasing the antiseptic agent contained therein which is then absorbed by the applicator pad. The defeatable barrier or membrane is also removable or may be defeated in connection with other mechanisms according to various embodiments.

8 Claims, 14 Drawing Sheets

(56) References Cited

U.S. PATENT DOCUMENTS

| | | | |
|---|---|---|---|
| 5,490,736 A * | 2/1996 | Haber | A61M 35/006 401/132 |
| 5,558,874 A | 9/1996 | Haber et al. | |
| 6,371,675 B1 | 4/2002 | Hoang et al. | |
| 6,916,133 B2 | 7/2005 | Hoang et al. | |
| 7,008,392 B2 | 3/2006 | Beaudry | |
| 8,123,423 B2 | 2/2012 | Houde et al. | |
| 8,696,227 B1 * | 4/2014 | Carter | A61M 35/006 401/132 |
| 2001/0055511 A1 | 12/2001 | Baumann et al. | |
| 2002/0076258 A1 | 6/2002 | Crosby et al. | |
| 2004/0068218 A1 | 4/2004 | Davis et al. | |
| 2004/0223801 A1 * | 11/2004 | Detwiler | A45D 34/04 401/132 |
| 2004/0240927 A1 | 12/2004 | Hoang et al. | |
| 2004/0267182 A1 * | 12/2004 | Davis | A61L 2/0088 604/2 |
| 2005/0265768 A1 * | 12/2005 | Tsaur | A45D 34/02 401/133 |
| 2006/0247568 A1 * | 11/2006 | Stenton | A61M 35/003 604/3 |
| 2009/0093746 A1 * | 4/2009 | Nacer | A61F 13/38 604/3 |
| 2009/0324320 A1 | 12/2009 | Houde et al. | |
| 2011/0066121 A1 | 3/2011 | Hoang et al. | |
| 2012/0141186 A1 | 6/2012 | McDonald | |
| 2013/0156485 A1 | 6/2013 | Guzman | |
| 2013/0156486 A1 | 6/2013 | Guzman et al. | |

* cited by examiner

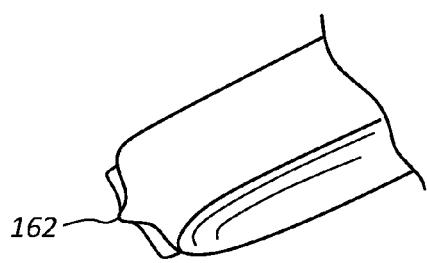 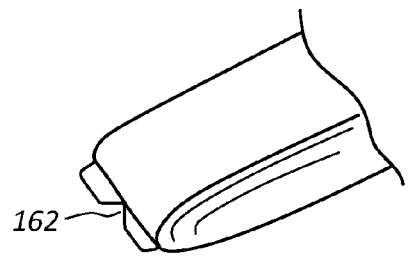
FIG. 13A  FIG. 13B
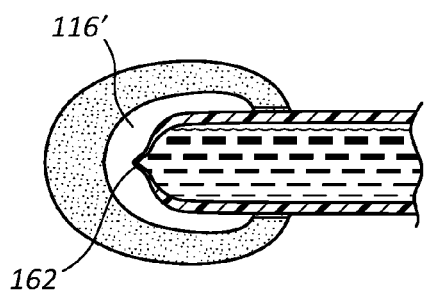 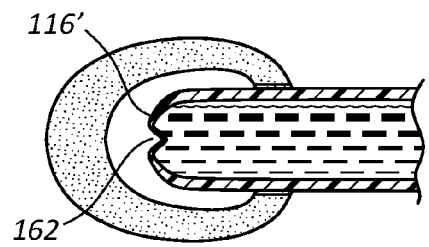
FIG. 13C  FIG. 13D
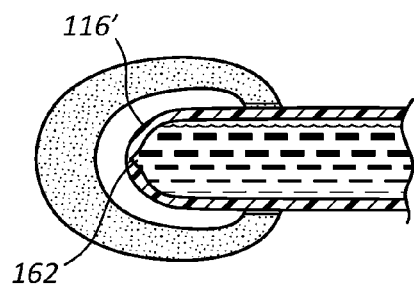 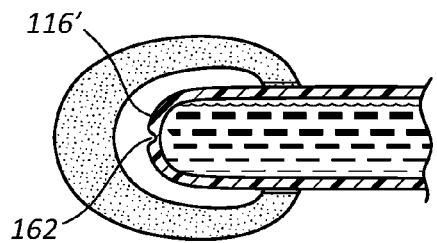
FIG. 13E  FIG. 13F

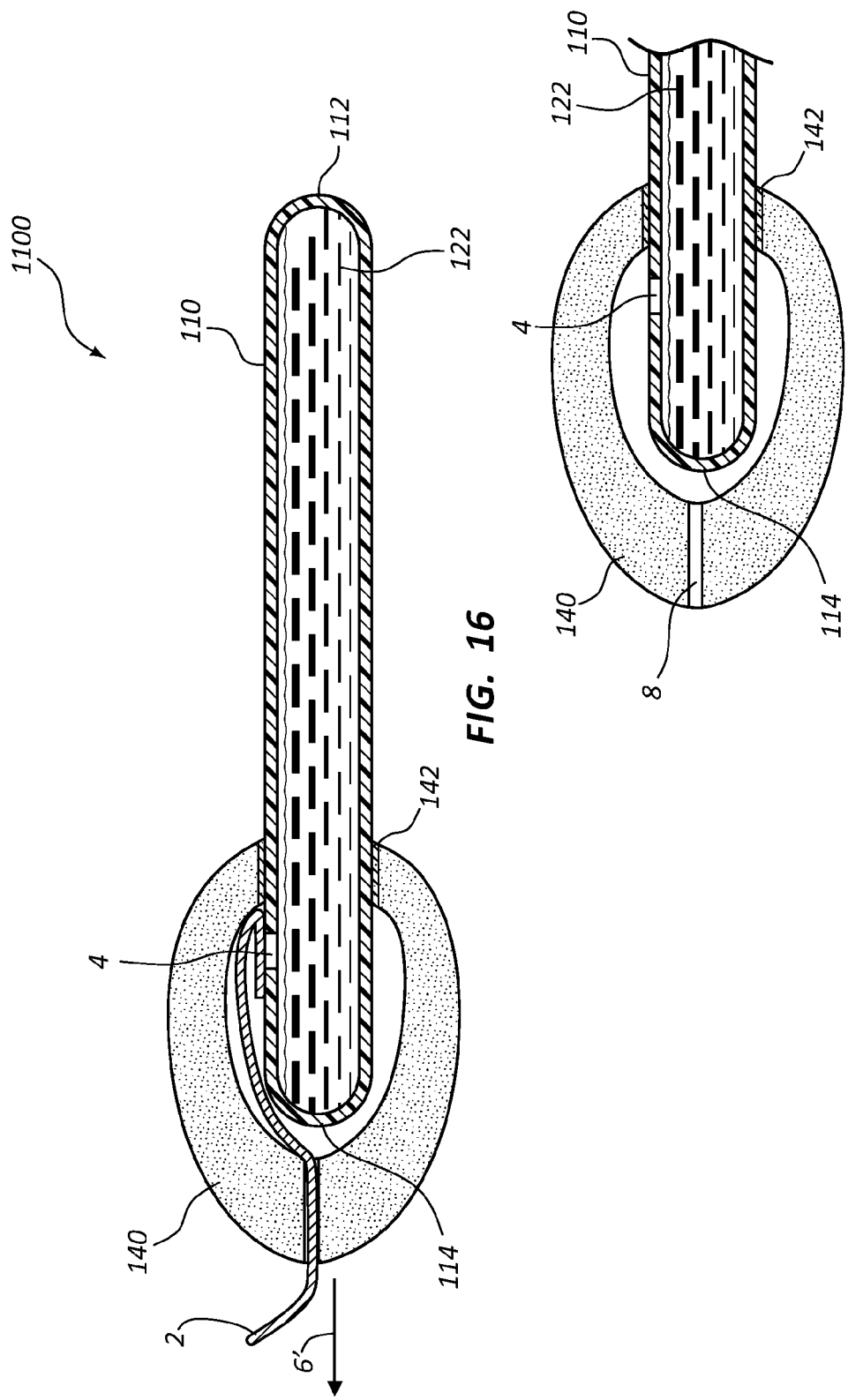

SYSTEMS AND METHODS FOR PROVIDING AN ANTIMICROBIAL DISPENSING APPLICATOR

FIELD OF THE INVENTION

The present invention relates to systems and methods for providing an antiseptic or antimicrobial dispensing applicator. An antiseptic or antimicrobial dispensing applicator is used to apply an antiseptic agent or an antimicrobial solution to a desired surface thereby preparing the surface for a procedure or treatment.

BACKGROUND OF THE INVENTION

Healthcare Associated Infections (HAIs) are a major patient safety and hospital problem, frequently associated with surgical sites and invasive devices, such as vascular access lines, urinary catheters, patient skin preparation prior to surgery, and ventilators. Accordingly, antiseptic, antibacterial and antimicrobial agents are commonly applied to various surfaces in preparation for sterile or antiseptic procedures. For example, a common pre-operative procedure in the medical industry involves rubbing alcohol, iodine, peroxide or chlorhexidine on a skin surface to kill bacteria and thus reduce the chance of infection. Other common practices include wiping down a chair or table surface with an antiseptic agent prior to exposing a patient or instruments to the surface. Other common uses of antiseptics is in the treatment of various injuries, such as cuts and abrasions.

Typically, an applicator, such as a cotton swab, a swab stick, a foam sponge pad, or a towelette, is soaked with an antiseptic that must be poured from a bottle or other container. This step requires that the user remove the lid of the container and the foil seal to access the antiseptic. In an emergency situation, or in a situation where one of the user's hands is occupied, the user is required to free both hands to access the antiseptic agent. Furthermore, once the bottle or other container is opened, the sterility of the bottle is compromised often resulting in excess waste of otherwise useful antiseptic agent. Alternatively, there are also concerns about the degradation or evaporation of active ingredients in the antiseptic solution in bulk.

Following these steps, the antiseptic is commonly poured into an open, secondary container which provides a pool into which the applicator is dipped or soaked. The open, secondary container may include a dish or small bowl having a large opening through which the applicator is passed. In an emergency situation the user must take caution to prevent bumping or disturbing the secondary container so as to prevent a spill of the antiseptic. In the event that the antiseptic agent is spilled, additional antiseptic must be provided thereby requiring the user to once again access the container or bottle of antiseptic.

In other procedures, an antiseptic agent is applied directly to a surface from the bottle or other container, and is then spread and applied with the applicator. During these procedures, the user must take precautions to control the amount of antiseptic used so as to contain the antiseptic and avoid wasting materials.

For some procedures, a portion of the applicator that contacts the desired surface is held directly in the hand of the user. For example, where the applicator is a wipe or towelette and the surface is a tabletop, the user generally holds the wipe in their hand and rubs the surface with the wipe. The proximity of the user's hand to the table surface presents the danger of contaminating the newly sanitized surface with the user's hand. While the user may choose to wear protective gloves or wash their hands prior to applying the antiseptic, in an emergency situation the user may not have sufficient time to take the necessary precautions.

By way of another example, swab applicators or swab sticks are commonly provided as dry devices containing no antiseptic solution. They are provided in individual or bulk packing containing, for example, one, three, ten, fifty, or a hundred units. Swab sticks are typically used by either dip-soaking the stick in a bulk bottle of antiseptic or applying antiseptic onto a patient's skin first and then using the swab stick to spread the antiseptic. Beyond the challenges already discussed above, the bulk packaging of swab sticks may result in contamination to unused swab sticks every time the common container is accessed. Moreover, even where swab sticks are pre-soaked with antiseptic, the amount cannot be controlled, there are concerns about degradation or effectiveness loss of antiseptics due to prolonged contact between the antiseptics and the material of the applicator pad, and the antiseptics often cover the entire swab stick thereby coming in unwanted contact with the user during use of the swab stick.

Thus, while techniques currently exist that are used for applying an antiseptic agent to a desired surface, challenges still exist. Accordingly, it would be an improvement in the art to augment or even replace current techniques with other techniques.

BRIEF SUMMARY OF THE INVENTION

The present invention relates to a safe and convenient handheld applicator device for delivering an antiseptic solution to a desired surface. Some embodiments of the present invention provide an applicator device including a body having a lumen for receiving an antiseptic agent. According to some embodiments, the body is generally composed of a soft, flexible, or semi-flexible polymer material capable of being compressed, squeezed, folded, or twisted by a user. In other embodiments, the body is composed of a rigid or semi-rigid polymer material. According to some embodiments, the rigid or semi-rigid polymer materials comprising the device are capable of being compressed or squeezed by a user. One end of the lumen defined by the body is configured to receive a fluid and thereby acts as a reservoir containing a desired antiseptic solution. At the other end of the body, the device includes an applicator pad for absorbing and applying the antiseptic solution to a desired surface. The applicator pad generally includes a non-woven or foam pad material suitable for applying the antiseptic solution.

A defeatable membrane or barrier is interposed between the lumen of the body and the applicator, such that the antiseptic agent is prevented from contacting the applicator prior to activation. In some embodiments, the device further includes various activation mechanisms whereby, upon activating the device, the membrane or barrier is defeated thereby permitting the antiseptic agent to flow through the membrane and contact the applicator pad. According to some embodiments, the membrane is defeated by simply compressing the body of the device to increase the pressure within the lumen. The increased pressure is released as the membrane is defeated and the antiseptic agent is permitted to flow through the membrane. In other embodiments, the membrane is defeated by twisting the body of the device in order to sufficiently increase the pressure therein. In still other embodiments, the membrane is replaced with a one-way valve that is defeated by increasing the pressure within the lumen of the body. In yet additional embodiments, the membrane is broken or ruptured by user operation of a rupturing mechanism or user application of partially and predictably destructive opposing torsional forces.

In some embodiments, the membrane separating the tube chamber and the applicator pad is provided with a plastic weld or adhesive seam and is broken by lateral force on the membrane near the applicator pad to allow the antimicrobial solution to flow from the tube chamber to the sponge pad. The thickness of the membrane can be varied depending on the force desired to break the membrane.

In some embodiments of the present invention, the applicator is shaped and configured to apply the antiseptic agent to an orifice, such as a mouth or a respirator tube. In other embodiments, the applicator is shaped and configured to apply the antiseptic agent to a generally flat surface such as an I.V. insertion site, a surgical procedure site, or a table.

According to some embodiments, the present invention comprises swab sticks containing antiseptic solution. In such embodiments, the applicator tube is made of soft, flexible, semi-flexible, rigid, or semi-rigid plastic materials. As above, the body of the applicator tube defines a chamber which operates as an antiseptic reservoir. Prior to activation, the reservoir chamber is sealed from the applicator head but has a breakable or defeatable membrane interposed therein designed to be broken or opened easily by squeezing the body of the stick tube. In some embodiments, the defeatable membrane is formed within a wall of the body. Upon activation, the antiseptic flows into the applicator head pad. In some embodiments, the dosage of antiseptics provided is pre-specified and controlled. According to various embodiments, the antiseptic dispensing applicators can be single-packaged or triple-packaged to avoid cross-contamination.

For some implementations of the present invention, additional activation mechanisms are contemplated. For example, in some embodiments, the present invention includes a roller clamp mechanism or actuator configured for manual operation, such as by a user's thumb. In other embodiments, as mentioned above, a pinching or rupturing mechanism in incorporated into the device to facilitate the release of antiseptic fluid from the lumen defined by the body of the device. In still other embodiments, a removable seal is contemplated for temporarily sealing the device, wherein the device is activated as the seal is removed.

Finally, in some embodiments, the device includes a membrane having a scored surface that is partially defeated in response to lateral force. As the lateral force is increased, additional portions of the membrane are defeated thereby permitting increased flow of the antiseptic agent through the membrane. In other embodiments, the membrane includes a plurality of scorings having various thicknesses and dimensions to progressively defeat the membrane in response to progressive increases in lateral force against the membrane.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. These drawings depict typical embodiments of the invention and are not therefore to be considered to limit the scope of the invention.

FIG. 13A is a side elevation view in cross section of an antiseptic dispensing applicator device having a weakly sealed tube portion in accordance with another representative embodiment of the present invention.

FIG. 13B is a side elevation view in cross section of an antiseptic dispensing applicator device having a weakly sealed tube portion in accordance with another representative embodiment of the present invention.

FIG. 13C is a side elevation view in cross section of an antiseptic dispensing applicator device having a weakly sealed tube portion in accordance with another representative embodiment of the present invention.

FIG. 13D is a side elevation view in cross section of an antiseptic dispensing applicator device having a weakly sealed tube portion in accordance with another representative embodiment of the present invention.

FIG. 13E is a side elevation view in cross section of an antiseptic dispensing applicator device in accordance with another representative embodiment of the present invention.

FIG. 13F is a side elevation view in cross section of an antiseptic dispensing applicator device in accordance with another representative embodiment of the present invention.

FIG. 16 is a side elevation view in cross section of an antiseptic dispensing applicator device having an alternative removable pull-tab seal in accordance with an alternative representative embodiment of the present invention.

FIG. 16A is a side elevation view in cross section of the device of FIG. 16 having the alternative removable pull-tab seal removed in accordance with another representative embodiment of the present invention.

DETAILED DESCRIPTION OF THE INVENTION

The presently preferred embodiments of the present invention will be best understood by reference to the drawings, wherein like reference numbers indicate identical or functionally similar elements. It will be readily understood that the components of the present invention, as generally described and illustrated in the figures herein, could be arranged and designed in a wide variety of different configurations. Thus, the following more detailed description, as represented in the figures, is not intended to limit the scope of the invention as claimed, but is merely representative of presently preferred embodiments of the invention.

As used herein, the term "proximal" refers to a location with respect to the device during normal use that is closest to the clinician and farthest from the patient. Conversely, the term "distal" refers to a location with respect to the device during normal use that is farthest from the clinician and closest to the patient. As used herein, the term "top", "up" or "upwardly" refers to a location with respect to the device during normal use that is radially away from the longitudinal axis of the device and away from the patient's skin. Conversely, as used herein, the term "bottom", "down" or "downwardly" refers to a location with respect to the device during normal use that is radially away from the longitudinal axis of the device and toward the patient's skin. As used herein, the term "in" or "inwardly" refers to a location with respect to the device during normal use that is toward the inside of the device. Conversely, as used herein, the term "out" or "outwardly" refers to a location with respect to the device during normal use that is toward the outside of the device.

Figure 1:
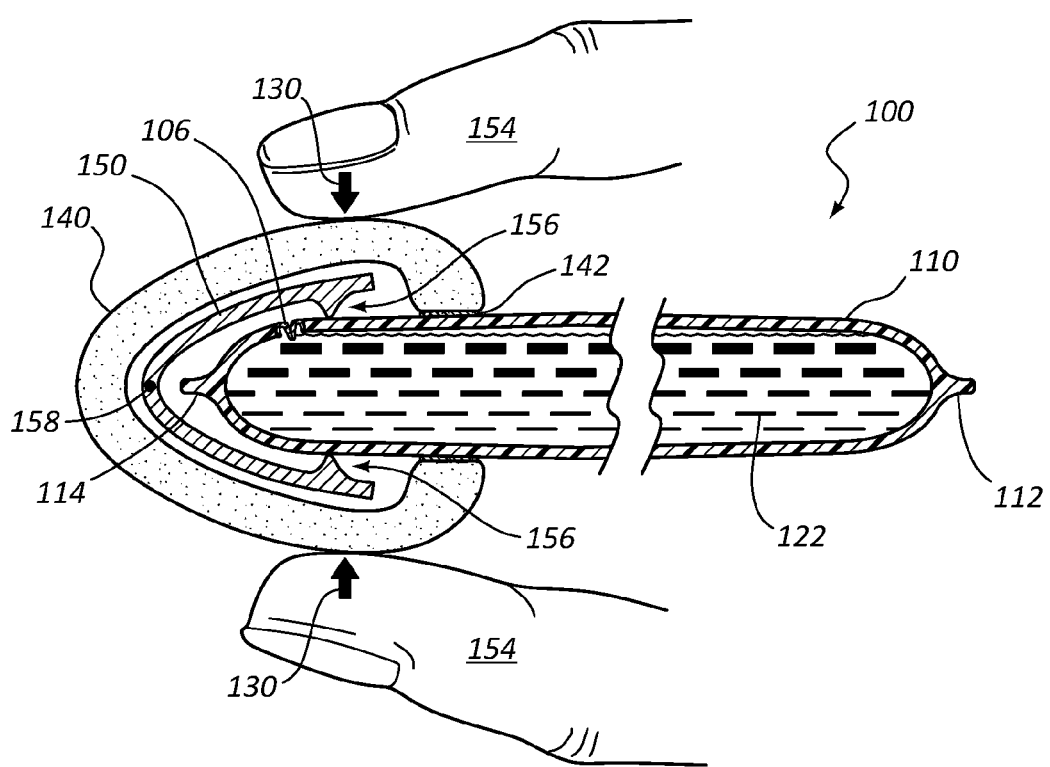
FIG. 1 is a side elevation view in cross section of an antiseptic dispensing applicator device having an internal pinching actuator in accordance with a representative embodiment of the present invention.

Referring now to FIG. 1, an implementation of an antiseptic dispensing applicator device 100 in accordance with some embodiments is shown. Some embodiments of device 100 generally include a body (or applicator tube) 110, having a proximal end 112 and a distal end 114. Body 110 generally comprises a tube defining a lumen comprising a fluid reservoir to compatibly receive an antiseptic agent or an antimicrobial solution 122. In some embodiments, the fluid reservoir or chamber defined by body 110 contains approximately 0.3-50 mL of the antiseptic agent 122. In other embodiments, the fluid reservoir defined by body 110 contains an alcohol-based antimicrobial solution. According to various embodiments, body 110 is made of a polymer or plastic material, such as polypropylene (PP), polyethylene (PE), and the like, capable of being heat-sealed at ends 112 and 114. Body 110 is flexible according to some embodiments, semi-flexible according to other embodiments, semi-rigid according to other embodiments, and rigid according to still other embodiments. Persons of ordinary skill in the art will appreciate that the strength of a given heat seal can be controllably varied such that certain heat seals can be relatively weak by design while others are comparatively much stronger by design. (See also FIG. 9). In some embodiments, body 110 of device 100 comprises tubing material with sufficient flexibility so as to be capable of being compressed, squeezed, or folded by a user 154.

According to some embodiments, the position and length of body portion 110 is selected to provide a gripping surface to the device 100 and remove the user's hand from the distal area proximate an applicator pad 140. As such, the handle function of the body portion 110 provides the user with control over the device 100 while preventing undesired exposure and/or contamination to the treatment site or surface.

Some embodiments of device 100 generally include a swab or applicator pad 140 located proximate the distal end 114 of body 110, as illustrated. According to some embodiments, applicator pad 140 comprises a non-woven material or a foam sponge pad that is attached proximate the distal end 114 via an adhesive 142 that is compatible with the antiseptic agent 122. In some embodiments, applicator pad 140 is comprised of cotton or cotton blends. The size, shape, and texture of applicator pad 140 varies dependent upon the intended application or for applying the antiseptic agent 122 to a desired surface. For example, applicator pad 140 is sized and shaped for a variety of uses, such as an oral disinfectant device, a skin or surgical site disinfectant device, a point-of-use catheter disinfectant coating device, an I.V. or catheter access cleaning device, as well as other convenient hand-held antimicrobial delivery systems. In some embodiments, applicator pad 140 includes an abrasive outer surface to assist in scrubbing and disinfecting an object, such as a piece of machinery or a surface such as a table or bed surface. And in some embodiments, applicator pad 140 includes a smooth outer surface for applying the antiseptic agent 122 to disinfect a surface without harsh scrubbing. In yet other embodiments, applicator pad 140 comprises a layered applicator pad such that contaminated layers of the pad may be removed to provide a fresh, uncontaminated application surface.

In some embodiments, the fluid reservoir defined by body 110 includes a threaded portion (not shown) for threadedly coupling to compatible threads (not shown) located within applicator pad 140. In other embodiments, the fluid reservoir defined by body 110 is coupled to applicator pad 140 via a pressure fit, a mechanical interface, or an adhesive.

As mentioned above, device 100 and applicator pad 140 are sized and shaped for a variety of uses according to various embodiments. Occasionally, for example, the inner and/or outer surfaces of the mouth must be disinfected, for example, prior to the insertion of a respirator tube, a ventilator system, or other medical device into the mouth or throat. Accordingly, the shape and size of applicator pad 140 is designed to compatibly insert within the mouth of a patient. For example, an applicator pad 140 for use as a mouth disinfectant device may include an elongated dome shape having a base diameter that is easily inserted into the patient's mouth. An elongated dome shape eliminates any right angles that may otherwise prevent thorough and even contact between the applicator pad 140 and the natural, curved surfaces of the inner mouth. Additionally, in some embodiments, the outer surface of applicator pad 140 includes a small radius that permits application of the applicator to the inner and outer surfaces of a respirator tube or other medical device prior to inserting the device into the mouth of the patient.

Where device 100 is intended as a skin or surgical site disinfectant device, the shape and size of applicator pad 140 is selected to provide a broad, flat surface (not shown) to maximize contact between applicator pad 140 and a generally flat skin surface. Such a configuration is particularly suitable for preparing a surgical site prior to performing surgery and for preparing a patient's skin before insertion of a catheter or I.V.

In other embodiments, device 100 and applicator pad 140 may be configured so as to provide a suitable size and shape for providing antimicrobial coatings to I.V. and/or catheter tubing prior to insertion of the same into a target site. For example, in some embodiments, applicator pad 140 forms a hollow cylindania, forming an elongated, tubular crescent shape slightly larger than the outer diameter of the I.V. or catheter tubing to be coated. In other embodiments, applicator pad 140 forms a torus so as to completely surround the I.V. or catheter tubing during the coating process.

With continued reference to FIG. 1, various embodiments of device 100 also include a pinching actuator device 150, which pinching device is made of rigid materials capable of rupturing or puncturing the distal end 114 of body 110. Pinching device 150 is located adjacent distal end 114 inside applicator pad 140 but outside distal end 114 and is retained in its orientation and position by the interaction between applicator pad 140 and body 110. Pinching device 150 includes one or more edges 156. According to some embodiments, for example, edge(s) 156 are relatively sharp edge(s) or point(s) that can pierce or puncture tube 110 to release solution 122. In other embodiments, two or more opposing sharp edges 156 can be formed offset relative to the functional axis 158 of pincher 150 such that operation of pincher 150 by user 154 (applying lateral forces 130) results in the application of shear cutting forces to tube 110 to thereby rupture or open the distal end 114 thereof. In still other embodiments, distal end 114 comprises a seal that is ruptured when lateral force 130 is applied to body 110 via edges 156 of pincher 150. During operation of pincher 150, blunt edges 156 transfer lateral force 130 applied by user 154 so as to apply pressure to distal end 114 to thereby compromise, rupture, or otherwise open the seal at distal end 114.

By way of further explanation, in some embodiments, device 100 comprises a self-containing antiseptic applicator wherein the fluid reservoir defined by body 110 is pre-filled during the manufacturing process with antiseptic solution 122. In such embodiments, body 110 is pre-filled with antiseptic solution 122 after distal end 114 is heat-sealed but before proximal end 112 is heat-sealed such that the fluid reservoir defined by body 110 containing antiseptic solution 122 is separated or sealed from applicator pad 140 prior to use. Upon use, user 154 compresses pincher 150 by applying lateral forces 130 in order to compromise or defeat the membrane at distal end 114. Upon being defeated, antiseptic solution 122 is released from tube body 110 in order to saturate or moisten applicator pad 140 for disinfectant use. As mentioned above, in some embodiments, device 100 is configured to release antiseptic solution 122 by utilizing mechanisms such as shearing cut, puncturing, or hydraulic pressure. In other embodiments, alternative mechanisms, such as twisting mechanisms (discussed in greater detail below), are contemplated.

According to some embodiments, device 100 comes pre-packaged (not shown). In such embodiments, user 154 pinches the head of applicator pad 140 so as to compress pincher 150 while device 100 remains inside the packaging. After antiseptic solution 122 is released from tube body 110 in the manner previously described, user 154 removes device 100 from its package for use. In this way, the sterility of device 100 is not compromised prior to use.

In some embodiments, an antiseptic or antimicrobial solution 122 in accordance with the present invention includes a 50-95% alcohol solution which further includes additional antimicrobial agents such as CHG, PCMX, triclosan, octenidine, hexachlorophene, PVP-1, iodine, and/or quaterium compounds in the range of 0.05% to 5% w/w of the antimicrobial solution. The alcohol is generally selected from at least one of ethyl alcohol, isopropyl alcohol, n-propanol alcohol, and mixtures thereof. In some embodiments, the solution further contains dimethicone, glycerin, cationic polymer such as PVP, cellulose, docosanol, BTMS, behenyl alcohol and/or poloxamer. In a preferred embodiment, a base antimicrobial solution contains approximately 70% alcohol, 2% CHG and 28% USP purified water for skin or surgical site preparation, and 0.12% CHG in 11% alcohol and water for mouth disinfecting and oral care. One of skill in the art will appreciate that other ingredients, including those mentioned above, may be added to each of the base antimicrobial solutions to provide a desired antimicrobial or antiseptic agent 122 for a specific application.

With continued reference to FIG. 1, according to some embodiments, body 110 is vented at air vent 106 such that antiseptic agent or fluid 122 is permitted to flow out of the punctured or ruptured membrane proximate distal end 114 even when user applied forces 130 are withdrawn or relaxed. In this way, once body 110 has been preliminarily ruptured or punctured, antiseptic agent or fluid 122 is permitted to flow out of body 110 without compression or continued squeezing due to the lumen defined by body 110 being vented. In some embodiments, as illustrated, air vent 106 is distal the point at which body 110 is punctured or otherwise ruptured. For example, in some embodiments, vent 106 is located proximal relative to the tip of distal end 114 but distal the point at which body 110 is punctured. In other embodiments, air vent 106 may be located at any suitable location, including adjacent the proximal end 112 of body 110. According to various embodiments, air vent 106 permits body 110 to be vented without creating a vacuum or otherwise pulling previously dispensed fluid 122 back into the lumen defined by body 110 when forces 130 are withdrawn or relaxed.

In various embodiments, air vent 106 comprises a one-way air valve. In such embodiments, vent 106 maintains the integrity of body 110 such that, prior to activation, fluid 122 is retained within the lumen defined by body 110. Upon activation of the device, fluid 122 is released at the puncture point(s) associated with edges 156. When forces 130 are subsequently reduced or eliminated, vent 106 permits air to flow into the lumen defined by body 110. According to some embodiments, a one-way air valve 106 generally comprises a flexible or semi-flexible polymer material that is secured within body 110. In some embodiments, the one-way air valve 106 includes a slit, a duck bill, or an umbrella valve. For example, in some embodiments, the one-way air valve 106 includes a slit that is biased to a closed position when outward force or pressure is exerted thereon from within the lumen defined by body 110 so as to prevent a fluid pathway there through. However, as discussed and disclosed herein, when a reverse or inward pressure is exerted on air vent 106, the one-way valve is defeated such that the slit opens to provide air communication from outside body 110 to the inside thereof. It is contemplated that vent 106 may be employed with any or all of the various embodiments disclosed herein.

In still other embodiments, air vent 106 comprises a dual direction air vent. According to some embodiments, for example, air vent 106 is formed of a micro porous hydrophobic material, such as Tyvek.

Figure 2A:
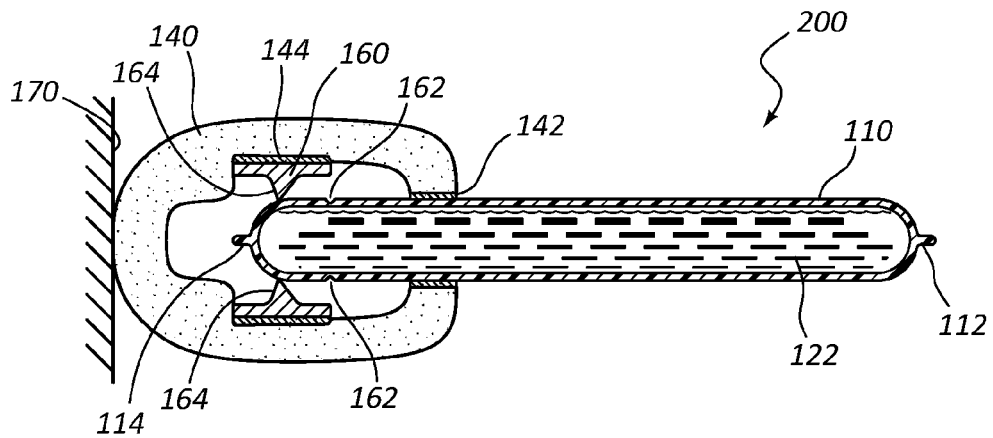
FIG. 2A is a side elevation view in cross section of an antiseptic dispensing applicator device (prior to activation) having a weak area in accordance with another representative embodiment of the present invention.

Referring now to FIGS. 2A-2F, various alternative embodiments of an antiseptic dispensing applicator device employing a body having one or more defeatable zones(s) or rupture point(s) forming a defeatable barrier in accordance with representative embodiments of the present invention are shown. With reference to FIG. 2A, a cross-sectional view of an antiseptic dispensing applicator device 200 having defeatable barriers 162 defining a weak area in accordance with some embodiments is shown. FIG. 2A depicts device 200 prior to activation. In some embodiments, one or more defeatable barrier(s) 162 may be located at any suitable locality on distal end 114 of body 110 (see also FIG. 2D) so long as defeatable barrier(s) 162 are located within the region of body 110 enclosed by applicator pad 140 such that, upon use, antiseptic fluid 122 is released from tube body 110 in order to saturate or moisten applicator pad 140 for disinfectant use. In other embodiments, defeatable barriers 162 comprise a weakened area, such as a circumferential groove or annulus that traverses the outer diameter of body 110 (see FIG. 2C). In still other embodiments, points, scoring, groves, lines, or cross-hatching patterns are formed in and/or around distal end 114 so as to diminish the structural integrity thereof thereby rendering distal end 114 in a weakened state so as to encourage distal end 114 to break or defeat in a predictable manner in response to increased pressure within body 110 (see FIGS. 2E and 2F).

With respect to some embodiments, defeatable barriers 162 comprises a defeatable membrane interposed between the lumen of body 110 and applicator pad 140, such that antiseptic agent 122 is prevented from contacting applicator pad 140 prior to activation. According to some embodiments, defeatable barrier(s) 162 is/are formed in one or more wall(s) of body 110 proximate the distal end thereof.

In various embodiments, the one or more defeatable barrier(s) 162 can take various patterns as illustrated in FIGS. 2A-2F. Moreover, defeatable barrier(s) 162 can be pre-formed in body 110 via laser cutting or laser drilling, ultrasonic cutting, using a heated blade or pin, or otherwise formed during the manufacturing and assembly process. In still other embodiments, defeatable barriers 162 are pre-formed by scoring body 110 such that the wall thickness of body 110 is weakened in a predictable pattern, which weakened pattern defines defeatable barrier 162.

Some embodiments of device 200 further generally include a retention ring 160 located proximate the distal end 114 of body 110 as illustrated. According to some embodiments, retention ring 160 is comprised of a rigid plastic material having protruding tabs, bumps, or arête type formations 164. Retention ring 160 is located adjacent distal end 114 inside applicator pad 140 but generally on the distal side of the pre-cut groove or defeatable barrier 162 and is retained in its orientation and position by the interaction and adhesive 142 between applicator pad 140 and body 110 as well as additional adhesive 144 between applicator pad 140 and retention ring 160.

Figure 2B:
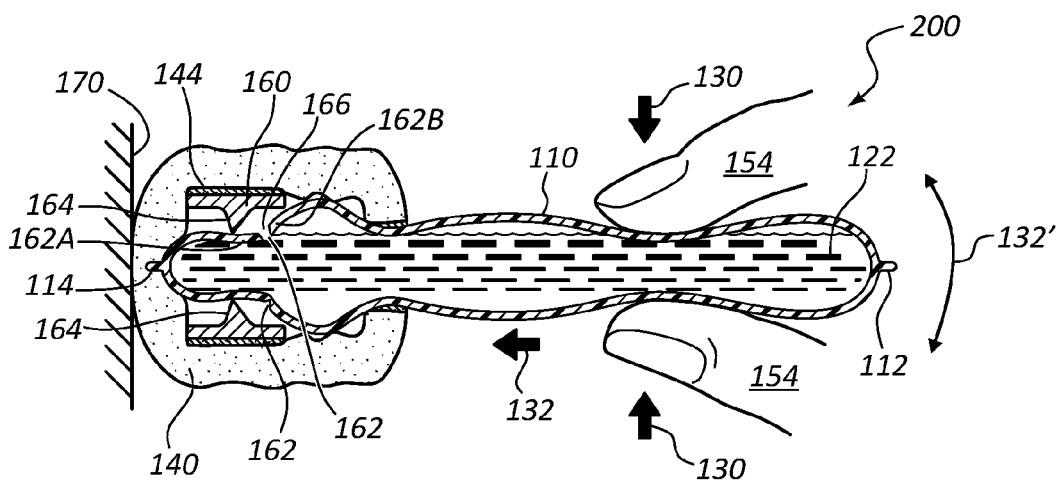
FIG. 2B is a side elevation view in cross section of the antiseptic dispensing applicator device of FIG. 2A following activation in accordance with a representative embodiment of the present invention.
Figure 2C:
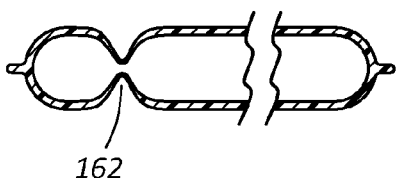
FIG. 2C is a side elevation view in cross section of the tube portion of an antiseptic dispensing applicator device having an alternative weak area in accordance with another representative embodiment of the present invention.

By way of further explanation, in some embodiments, device 200 comprises a self-containing antiseptic applicator wherein the fluid reservoir defined by body 110 is pre-filled during the manufacturing process with antiseptic solution 122. Upon use, user 154 holds device 200 against a flat surface 170 at the distal surface of applicator pad 140. As depicted in FIG. 2B, user 154 continues by applying an axial force to tube body 110 in the direction 132 thereby pushing tube body 110 toward flat surface 170 as well as the distal end of applicator pad 140. As user 154 continues to apply axial force in direction 132, thereby displacing body 110 axially, retention ring 160 is oriented such that bumps 164 are located just distally of defeatable barriers or grooves 162. User 154 continues by applying lateral forces 130 to tube body 110, which comprises a sufficiently rigid but semi-flexible tubing material capable of being compressed or squeezed by user 154 while simultaneously having axial force 132 applied thereto. As user 154 laterally squeezes body 110, liquid solution 122 is pushed in the distal direction thereby resulting in the transfer of user-generated pressure throughout body 110. As the internal hydraulic pressure increases, region 162B expands while region 162A is substantially held in place, or held in a pre-activation position, via retention ring 160 and tabs 164. In some embodiments, tabs 164 generally retain the radial dimension of body 110 against expansion or enlargement during activation of device 200. User 154 continues to apply lateral forces 130 and axial forces 132 until defeatable barrier 162 fails or ruptures due to stress concentrations under shear load thus resulting in opening 166.

FIG. 2B depicts device 200 following activation. Following activation, and upon the defeat of defeatable barrier 162, antiseptic solution 122 is released from tube body 110 via opening 166 in order to saturate or moisten applicator pad 140 for disinfectant use. User 154 can continue to apply lateral force 130 as necessary to displace a sufficient or desired quantity of antiseptic solution 122 from body 110 into applicator pad 140.

Those of skill in the art will appreciate the relative thickness of the walls of body 110 and the depth of defeatable barrier or groove 162 both necessary and sufficient to accomplish the above-recited construction and operation of device 200.

According to various embodiments disclosed herein, a defeatable area formed within a wall of body 110, represented by defeatable barrier 162 in distal end 114, is interposed between the fluid contents of the reservoir defined by body 110 and applicator pad 140. Defeatable barrier 162 is provided to prevent fluid communication between the reservoir defined by body 110 and applicator pad 140 prior to activation or use. Defeatable barrier 162 comprises a scored or weakened area of body 110 so as to encourage defeatable barrier 162 to break or defeat in a predictable manner upon activation. In some embodiments, defeatable barrier 162 is located such that, as body 110 is actuated, shearing forces are applied to defeatable barrier 162 thereby causing defeatable barrier 162 to defeat along the scored pathway, as shown in FIG. 2B. Once defeated, opening 166 provides a fluid communication pathway between body 110 and applicator pad 140.

Figure 2D:
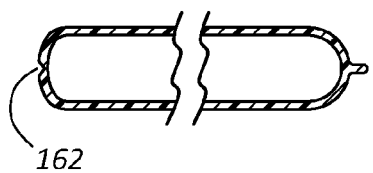
FIG. 2D is a side elevation view in cross section of the tube portion of an antiseptic dispensing applicator device having an alternative weak area in accordance with another representative embodiment of the present invention.
Figure 2E:
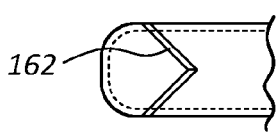
FIG. 2E is a side elevation view in cross section of the tube portion of an antiseptic dispensing applicator device having an alternative weak area in accordance with another representative embodiment of the present invention.
Figure 2F:
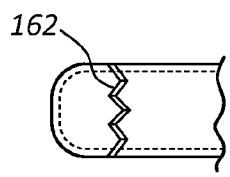
FIG. 2F is a side elevation view in cross section of the tube portion of an antiseptic dispensing applicator device having an alternative weak area in accordance with another representative embodiment of the present invention.

FIGS. 2C-2F illustrate additional embodiments of the present invention. Such embodiments function as generally described with reference to FIGS. 2A and 2B. As illustrated, defeatable barriers 162 may take a variety of shapes or configurations suitable for practicing the present invention. For example, the defeatable barrier 162 of FIG. 2C comprises an annular ring or groove formed around the circumference of body 110 at the distal end thereof. Alternatively, FIG. 2D illustrates a defeatable barrier 162 comprising a weakened point located at the distal extremity or face of body 110. FIG. 2E illustrates yet another embodiment wherein defeatable barrier 162 comprises scoring the distal end of body 110 with a predictable failure pattern. Similarly, FIG. 2F illustrates an alternative scoring pattern forming defeatable barrier 162.

Figure 3:
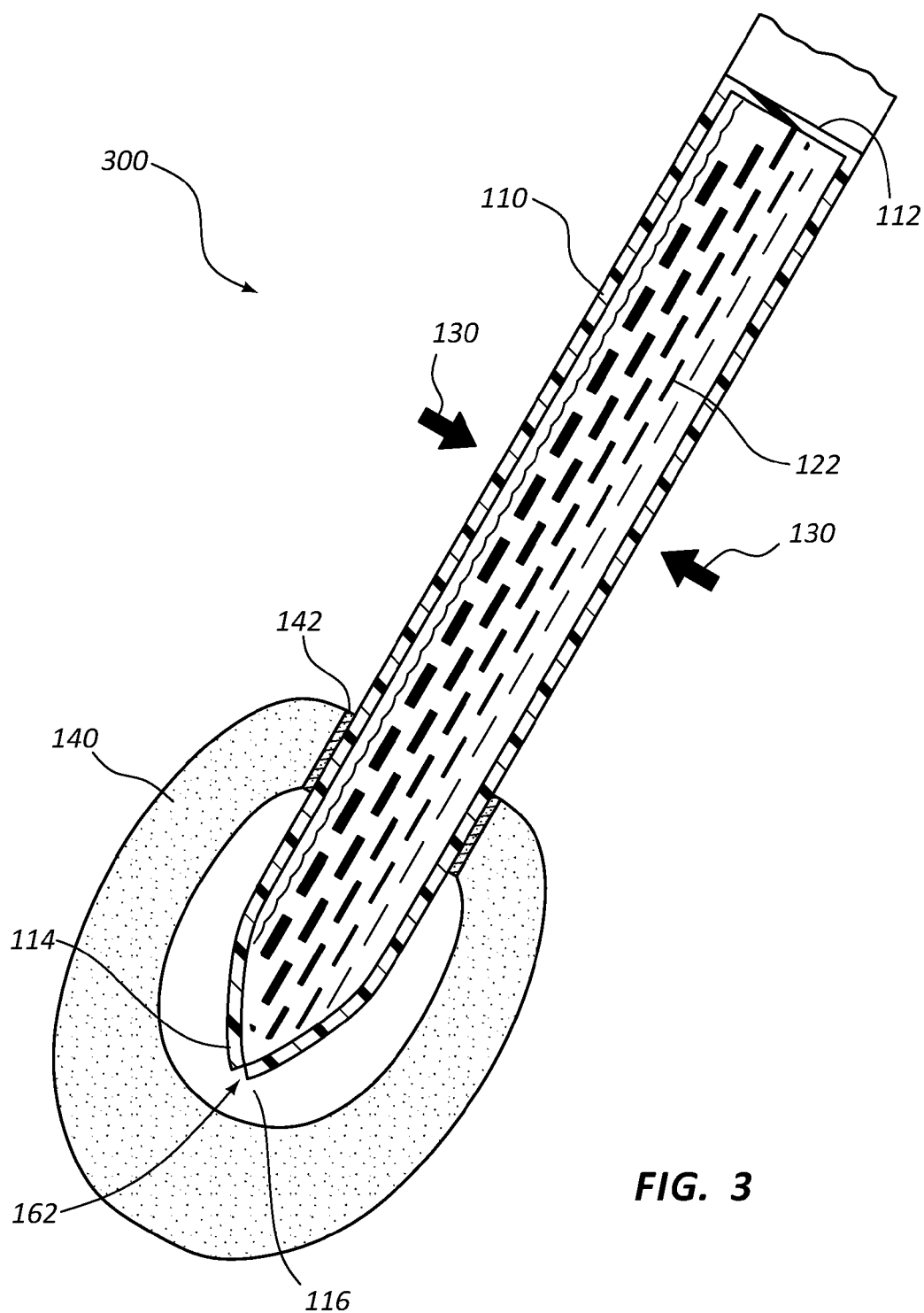
FIG. 3 is a side elevation view in cross section of an antiseptic dispensing applicator device having a weak point and a cone-shaped tip in accordance with another representative embodiment of the present invention.

Turning now to FIG. 3, a cross-sectional view of an antiseptic dispensing applicator device 300 having a defeatable tip 162 positioned on a cone-shaped or narrowing, pointed distal end 114 in accordance with some embodiments is shown. In such embodiments, the tip 116 of tube body 110 includes a scored surface that may be defeated in response to increased internal fluid pressure. As in other embodiments, device 300 comprises a self-containing antiseptic applicator having a fluid reservoir defined by body 110 that is pre-filled with antiseptic solution 122. Upon use, a user applies lateral forces 130 to tube body 110 near the proximal end 112 thereof. In such embodiments, body 110 comprises a semi-flexible tubing material capable of being compressed or squeezed by a user while simultaneously having sufficient axial rigidity so as to substantially maintain its axial shape and dimension. As a user laterally squeezes body 110, liquid solution 122 is pushed in the distal direction thereby resulting in the transfer of user-generated pressure throughout body 110. Once the internal hydraulic pressure is large enough to overcome the structural integrity of the defeatable tip 162, tip 116 of the cone-shaped distal end 114 ruptures due to stress concentrations at the defeatable tip 162. Persons of skill in the art will appreciate the manner of determining the required pressure, tube body 110 thickness, and radius necessary to cause the body 110 material to yield as desired. Following activation and the defeat of defeatable tip 162, antiseptic solution 122 is released from tube body 110 via an opening (not shown) in order to saturate or moisten applicator pad 140 for disinfectant use. A user can continue to apply lateral force 130 as necessary to displace a sufficient or desired quantity of antiseptic solution 122 from body 110 into applicator pad 140.

As mentioned above, persons of skill in the art will appreciate the manner of determining the required pressure, tube body 110 thickness, and radius necessary to cause the body 110 material to yield as desired. The following mathematical equations or formulas are generally applicable relative to various embodiments disclosed herein, as will be understood by persons of ordinary skill in the art:

$\tau = F/A = F/(t \times L)$, where $\tau$ represents the shear stress expressed as the shear load F (proportional to internal pressure p) divided by the cross-sectional area A expressed as thickness of the tube t multiplied by the length of the defeatable barrier L that is under shear.

$\sigma_1 = (pr^2/(R^2-r^2))(R^2/x^2+1)$ and $\sigma_3 = -(pr^2/(R^2-r^2))(R^2/x^2-1)$, where $r \leq x \leq R$, and where the hoop stress $\sigma_1$ and the radial stress $\sigma_3$ are expressed relative to internal pressure p, outer radius of the tube R, and inner radius of the tube r, and the hoop and radial stress both reach their maximum when x=r and decrease as x approaches R.

$\sigma_1 = pr/t$, where $\sigma_1$ is the approximate hoop stress for a cylinder according to thin-wall tube theory, and p is the internal pressure, r is the inner radius of the tube and t is the tube wall thickness.

$\sigma_1 = pr/2t$, where $\sigma_1$ is the approximate hoop stress for a sphere according to thin-wall tube theory, and p is the internal pressure, r is the inner radius of the tube and t is the tube wall thickness.

Figure 4A:
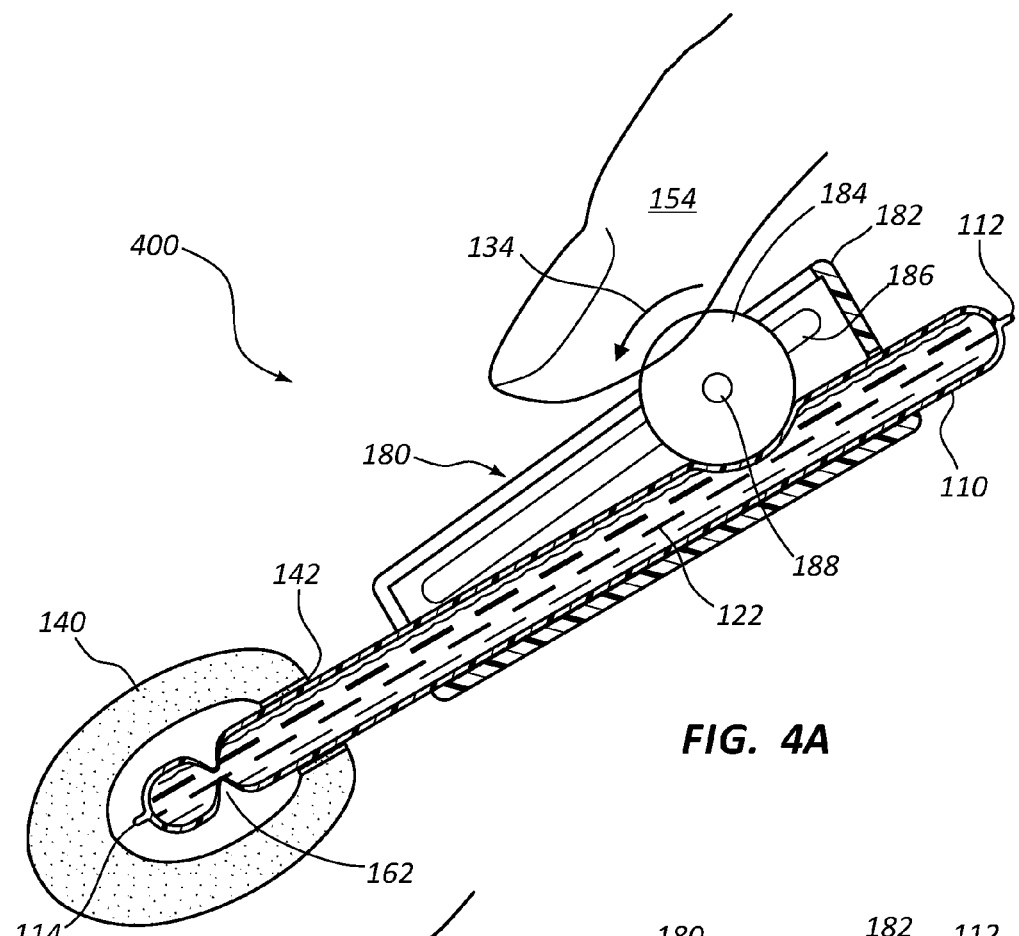
FIG. 4A is a side elevation view in cross section of an antiseptic dispensing applicator device (prior to activation) having a roller clamp actuator in accordance with another representative embodiment of the present invention.
Figure 4B:
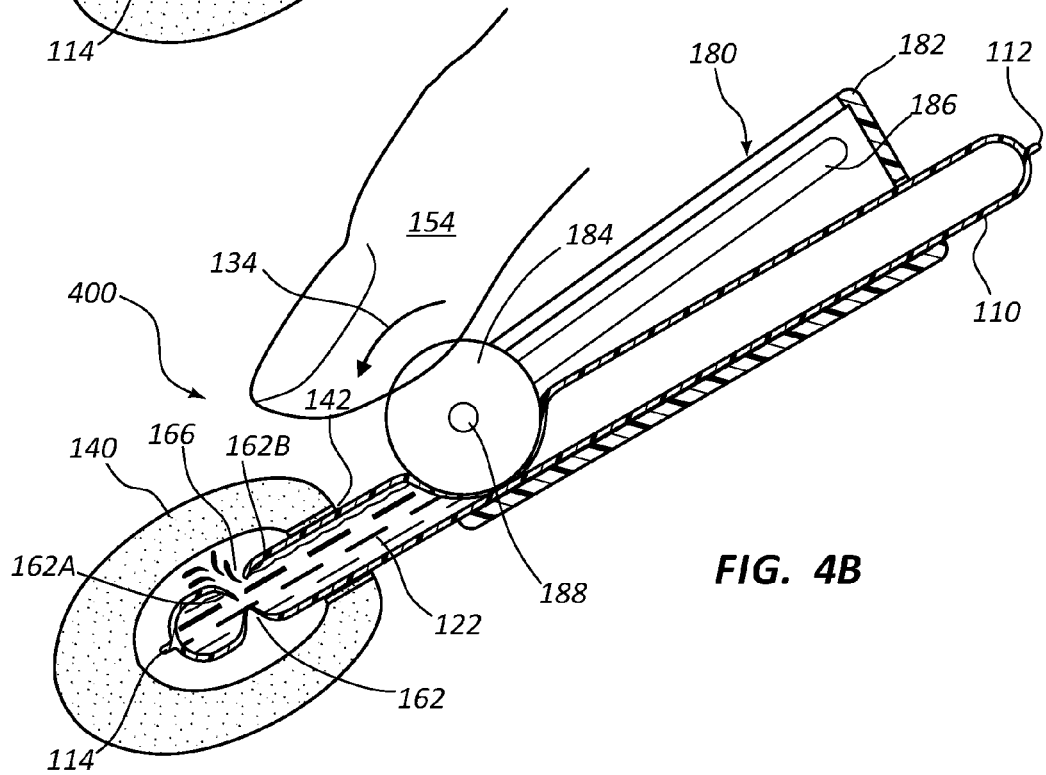
FIG. 4B is a side elevation view in cross section of the antiseptic dispensing applicator of FIG. 4A following activation in accordance with a representative embodiment of the present invention.

Referring now to FIGS. 4A and 4B, an antiseptic dispensing applicator device having one or more weak area(s) or rupture point(s) and a roller clamp in accordance with various representative embodiments of the present invention is shown. With reference to FIG. 4A, a cross-sectional view of an antiseptic dispensing applicator device 400 having pressure sensitive defeatable barriers 162 defining a weak area in accordance with some embodiments is shown. In such embodiments, the one or more defeatable barriers 162 are similar to the weakened points, grooves, or areas discuss previously. FIG. 4A depicts device 400 prior to activation.

Some embodiments of device 400 further generally include a roller clamp assembly or actuator 180 located near the proximal end 112 of body 110 prior to activation as illustrated. According to some embodiments, roller clamp 180 further includes a slidable frame or mounting assembly 182, an axially configured rolling mechanism 184, a guide or groove 186, and an axle or roller shaft 188. In some embodiments, roller clamp assembly 180 is permanently slidably coupled or attached to body 110. In other embodiments, roller clamp assembly 180 is removable and reusable with multiple additional antiseptic dispensing applicator devices. Further, according to some embodiments, roller clamp assembly 180 is slidably mounted so as to fully close body 110 upon activation of roller clamp assembly 180. In other embodiments, roller clamp assembly 180 is configured to only partially close body 110 upon activation of roller clamp assembly 180. Body 110 comprises a semi-flexible tubing material capable of being compressed or squeezed in full or in part by roller clamp assembly. In some instances, rolling mechanism 184 is advanced manually to compress body 110, such as via the thumb of user 154. In other embodiments, rolling mechanism 184 is advanced via automated means, such as a small electric motor.

According to some embodiments, user 154 manually advances roller clamp assembly 180 by rotating rolling mechanism 184 distally in direction 134 to activate device 400. As roller clamp assembly 180 moves distally under the manual rotational force 134, the internal hydraulic pressure inside body 110 gradually increases and liquid solution 122 is pushed distally. Once the internal hydraulic pressure is large enough to overcome the structural integrity of the one or more defeatable barriers 162, distal end 114 ruptures due to stress concentrations at the defeatable barriers 162.

According to some embodiments, as the internal hydraulic pressure increases within body 110, region 162B expands while region 162A remains static owing to the shape and formation of the annulus groove or defeatable barrier 162, as shown in FIG. 4B. User 154 continues to advance roller clamp assembly 180 via application of rotational force 134 until defeatable barrier 162 fails or ruptures due to stress concentrations thus resulting in opening 166. Following activation, antiseptic solution 122 is released from tube body 110 via opening 166 and saturates or moistens applicator pad 140 for disinfectant use. User 154 may continue to apply rotational force 134 as necessary to displace additional antiseptic solution 122 from body 110 into applicator pad 140.

As illustrated in FIGS. 4A and 4B, guide or groove 186 is oriented relative to body 110 at an angle according to some embodiments. In such configurations, as roller clamp assembly 180 is advanced distally, the pressure within body 110 and the stress concentration at defeatable barrier 162 increases gradually until defeatable barrier 162 fails and antiseptic solution 122 escapes via opening 166.

Figure 5:
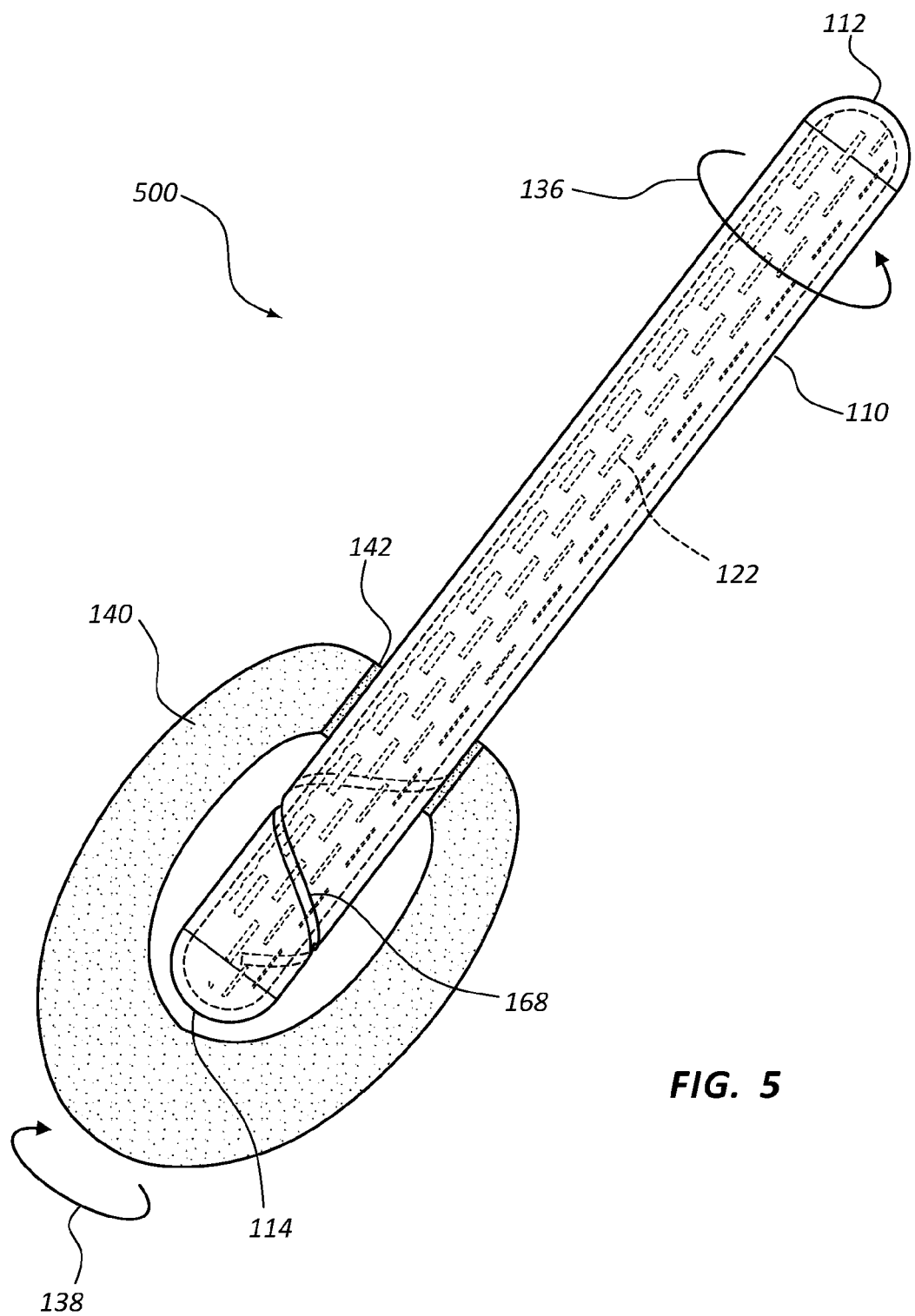
FIG. 5 is a side elevation view in cross section of an antiseptic dispensing applicator device having a twist-open configuration in accordance with another representative embodiment of the present invention.

Turning now to FIG. 5, an embodiment of an antiseptic dispensing applicator device 500 is shown comprising a helical score that is defeated by torsional force 136. As shown, device 500 includes various elements common to other embodiments, including body 110 that defines a fluid reservoir pre-filled with antiseptic fluid 122, proximal end 112, distal end 114, and applicator pad 140. As in other embodiments, body 110 is sealed prior to activation such that the fluid contents 122 of body 110 are not in fluid communication with applicator pad 140 prior to activation. In some embodiments, device 500 further includes a pre-cut helical groove 168 along body 110 located proximate the distal end 114 thereof. Helical groove 168 may is generally located within the region of body 110 enclosed by applicator pad 140 such that, upon use, antiseptic fluid 122 is released from tube body 110 in order to saturate or moisten applicator pad 140 for disinfectant use. Pre-cut helical groove 168 can be pre-formed in body 110 via laser cutting, laser drilling, ultrasonic cutting using a heated blade or pin, or otherwise formed during the manufacturing process. In some embodiments, helical groove 168 comprises a 45-degree (45°) helix.

Upon use, according to some embodiments, a user activates device 500 by manually applying opposing torsional forces 136 and 138 to tube body 110. In such embodiments, body 110 comprises a semi-rigid tubing material or materials. As a user applies opposing torsional forces 136 and 138, helical groove 168 is defeated in a predictable manner along the path defined by helical groove 168. Once defeated, antiseptic solution 122 is released from tube body 110 via the helical opening in order to saturate or moisten applicator pad 140 for disinfectant use.

According to some embodiments, device 500 comes pre-packaged. In such embodiments, a user activates device 500 by manually applying opposing torsional forces 136 and 138 to body 110 so as to create a fluid communication path between the fluid reservoir defined by body 110 and applicator pad 140 while device 500 remains inside the packaging. After antiseptic solution 122 is released from tube body 110 in the manner previously described, the user removes device 500 from its packaging for use. In this way, the sterility of device 500 is not compromised prior to use.

Figure 6:
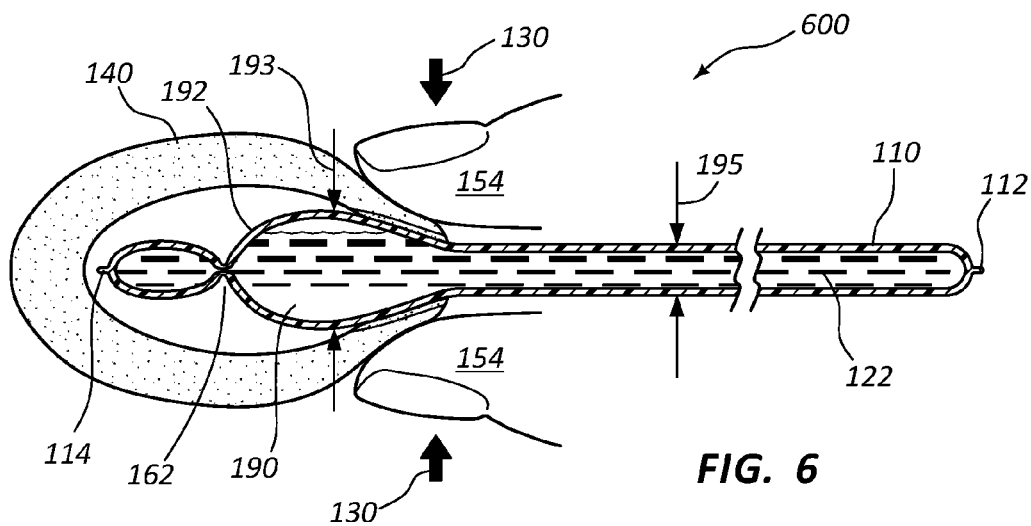
FIG. 6 is a side elevation view in cross section of an antiseptic dispensing applicator device having a distal squeeze chamber in accordance with another representative embodiment of the present invention.

With reference now to FIG. 6, another embodiment of an antiseptic dispensing applicator device 600 comprising a distal squeeze chamber 190 is illustrated. As shown, device 600 includes various previously discussed elements, including defeatable barrier 162. In some embodiments, device 600 further includes a distal squeeze chamber 190 located proximate the distal end 114 of body 110. Distal squeeze chamber 190 may be located anywhere along distal end 114 so long as the distal end 192 of distal squeeze chamber 190 is located generally within the region of body 110 enclosed by applicator pad 140 and proximal relative to defeatable barrier 162. User 154 activates device 600 by manually compressing distal squeeze chamber 190 to thereby apply lateral forces in direction 130 in order to increase internal hydraulic pressure and thereby compromise defeatable barrier 162 such that antiseptic solution 122 is released from body 110. In such embodiments, distal squeeze chamber 190 comprises a semi-flexible tubing material capable of being compressed or squeezed by user 154. Following activation, antiseptic solution 122 is released from body 110 to saturate or moisten applicator pad 140 for disinfectant use. As with other embodiments, device 600 is capable of being activated while contained within the manufacturer packaging such that the sterility of device 600 is not compromised prior to use. User 154 may continue to apply lateral force in direction 130 to displace additional antiseptic solution 122 from body 110 into applicator pad 140.

In some embodiments, distal squeeze chamber 190 is enlarged relative to body 110 such that distal squeeze chamber 190 has a larger diameter 193 than the diameter 195 of body 110 so as to restrict or discourage the flow of fluid 122 proximal of distal squeeze chamber 190 during compression of distal squeeze chamber 190. In some embodiments, body 110 is formed by a two-step process. In some embodiments, body 110 having diameter 195 is extruded. Then, according to various embodiments, body 110 is cut to length and subjected to a blow molding process to form diameter 193 of distal squeeze chamber 190.

Figure 7:
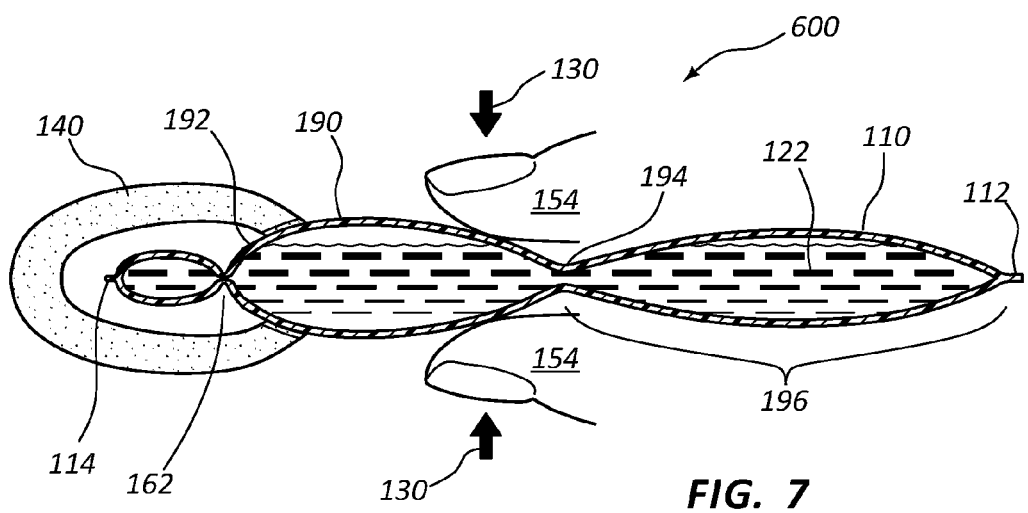
FIG. 7 is a side elevation view in cross section of an antiseptic dispensing applicator device having a liquid flow restrictor in accordance with another representative embodiment of the present invention.

FIG. 7 illustrates an alternative embodiment of device 600. Specifically, according to some embodiments, device 600 further includes a flow restrictor portion 194 formed in body 110. In such embodiments, body 110 of device 600 comprises tubing material with sufficient rigidity to maintain the flow restrictor 194 formation while being semi-flexible so as to be compressible or squeezable by user 154. Flow restrictor 194 is generally located at the axial midpoint of body 110 such that it is between squeeze chamber 190 and a proximal portion 196 of tube body 110. In various embodiments, flow restrictor 194 may be forward or aft of the axial midpoint of body 110. Flow restrictor 194 generally comprises a pinched or narrowed neck. In use, flow restrictor 194 restricts the proximal flow of antiseptic fluid 122 upon the application of lateral force in the direction 130 such that fluid 122 is forced distally causing defeatable barrier 162 to rupture in order to activate device 600.

Figure 8:
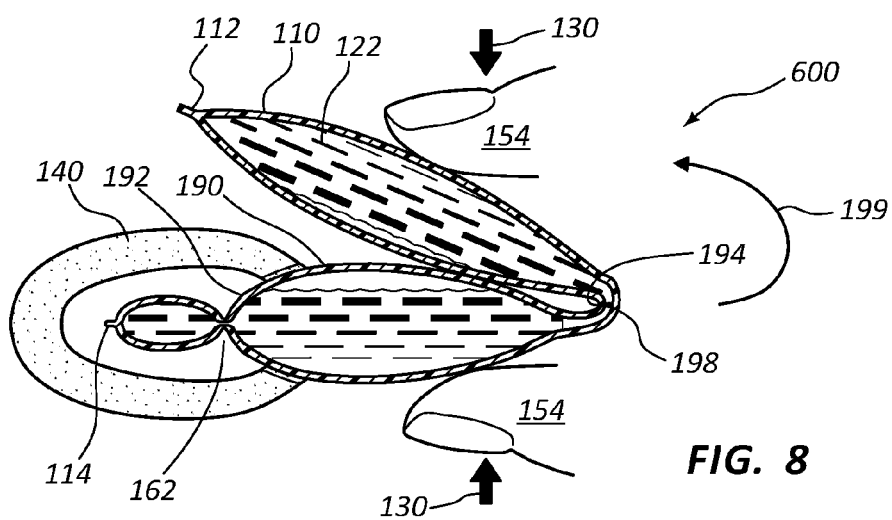
FIG. 8 is a side elevation view in cross section of a foldable antiseptic dispensing applicator device in accordance with another representative embodiment of the present invention.

FIG. 8 illustrates yet another variation on device 600 according to some embodiments of the present invention. As illustrated, according to some embodiments, flow restrictor portion 194 is generally flat so as to form a foldable axis 198 located at the approximate midpoint of body 110. As above, in some embodiments, flow restrictor 194 may be forward or aft of the axial midpoint of body 110. In such embodiments, body 110 of device 600 comprises semi-flexible tubing material with sufficient flexibility so as to permit user 154 to fold body 110 in the direction 199 such that body 110 folds at axis 198 and is capable of being compressed or squeezed in a folded orientation. In use, flow restrictor 194 restricts, or wholly eliminates, the proximal flow of antiseptic fluid 122 from squeeze chamber 190 upon the application of lateral forces in direction 130 such that fluid 122 is forced distally causing defeatable barrier 162 to rupture in order to activate device 600.

Figure 9:
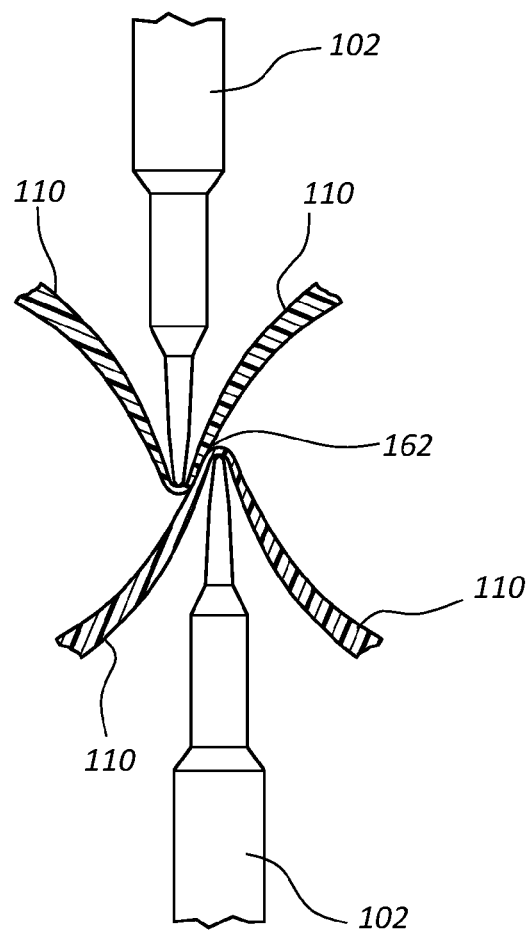
FIG. 9 is a side elevation view in cross section of a process for forming a weakly sealed tube portion of an antiseptic dispensing applicator device in accordance with various embodiments of the present invention.

Turning to FIG. 9, a method is disclosed for forming certain heat-seals, including defeatable barriers 162, at the distal end 114 of body 110 of devices 100, 200, 300, 400, 500 and 600 in accordance with various embodiments of the present invention. According to some embodiments, defeatable barrier 162 is formed using a set of heated elements 102 to press against distal end 114 of body 110 to thereby soften and partially melt the material of body 110 so as to form a joint therein. During this process, the material of body 110 is stretched at the joint and forms a defeatable barrier 162. In some embodiments, the wall thickness of body 110 at or near defeatable barrier 162 is smaller or thinner than in other areas. According to some embodiments, the set of heated elements 102 have an optimized offset, which is designed based on the wall thickness of tube body 110, the relevant material properties of the material comprising body 110, the desired width or shape of defeatable barrier 162, and other factors understood by those of skill in the art. The formation of defeatable barriers 162 in the manner set forth above facilitates the failure of defeatable barriers 162 as discussed herein.

Accordingly to some embodiments, heated elements 102 may be any desirable shape and/or dimensions, including a pin having a relatively blunt point, a square edge, a chamfered edge, a rounded edge, and any other desirable shape suitable to form a desired defeatable barrier 162. Additional plastic welding processes understood to those of skill in the art are contemplated herein.

Figure 10:
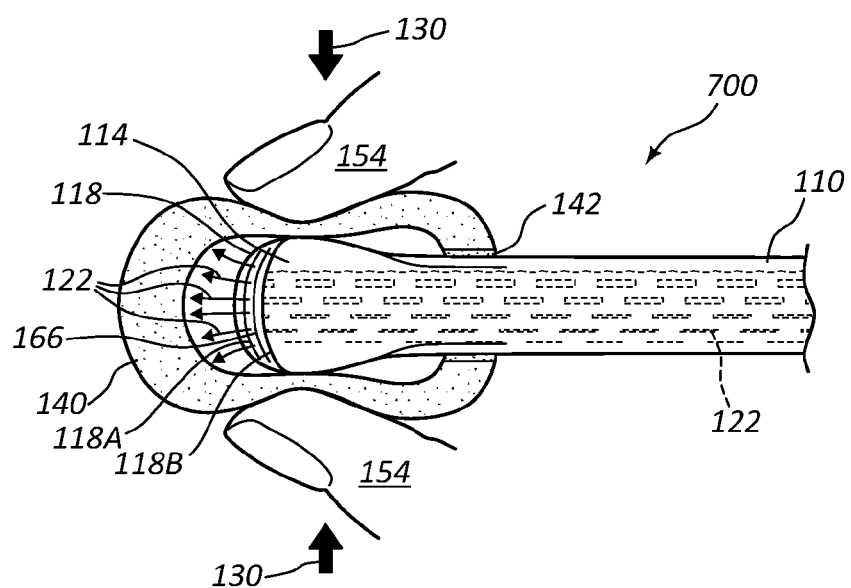
FIG. 10 is a perspective view in cross section of an antiseptic dispensing applicator device having a weakly sealed tube portion in accordance with another representative embodiment of the present invention.

Turning now to FIG. 10, another embodiment of an antiseptic dispensing applicator device 700 comprising a weakly sealed pop-open or squeeze-open distal tip 118 is shown. FIG. 10 depicts device 700 during or following activation. In some embodiments, body 110 is extruded or otherwise formed from a semi-rigid material. Distal end 114 of body 110 is cut to a desired shape, such as square, rounded or convex, chamfered, crescent or concave, or any other suitable shape. The two opposing sides of body 110 comprising 118A and 118B, respectively, are sealed. In some embodiment, sides 118A and 118B are sealed via plastic welding, adhesive, or other sealing means. The bond strength at sealed distal tip 118 is just enough to seal the tube body 110 and to sustain internal pressure from antiseptic solution 122 prior to activation.

User 154 activates device 700 by manually squeezing or compressing distal end 114 of body 110 until sufficient lateral forces are applied in direction 130 so as to overcome the bond strength of sealed distal tip 118. Once sufficient lateral forces are applied, the bond of sealed distal tip 118 is defeated such that sides 118A and 118B generally resume their pre-sealed orientation resulting in an open fluid pathway between the contents of the fluid reservoir defined by body 110 and applicator pad 140. In some embodiments, body 110 comprises a semi-flexible tubing material with sufficient structural rigidity or memory so as to bias sides 118A and 118B in their pre-sealed, open orientation after the bond of sealed distal tip 118 is defeated. In some embodiments, body 110 is further comprised of semi-flexible tubing material capable of being compressed or squeezed by user 154. In this manner, following activation of device 700 (as depicted in FIG. 10), antiseptic solution 122 is released from tube body 110 via opening 166 in order to saturate or moisten applicator pad 140 for disinfectant use. User 154 may continue to apply lateral force 130 to displace additional antiseptic solution 122 from body 110 into applicator pad 140. In other embodiments, device 700 is inverted to permit or otherwise encourage antiseptic agent 122 to flow into applicator pad 140 due to gravitational forces. Finally, it should be understood that a weakly sealed pop-open or squeeze-open distal tip 118 as shown and discussed can be employed on a variety of different embodiments previously discussed or otherwise disclosed herein.

Figure 11:
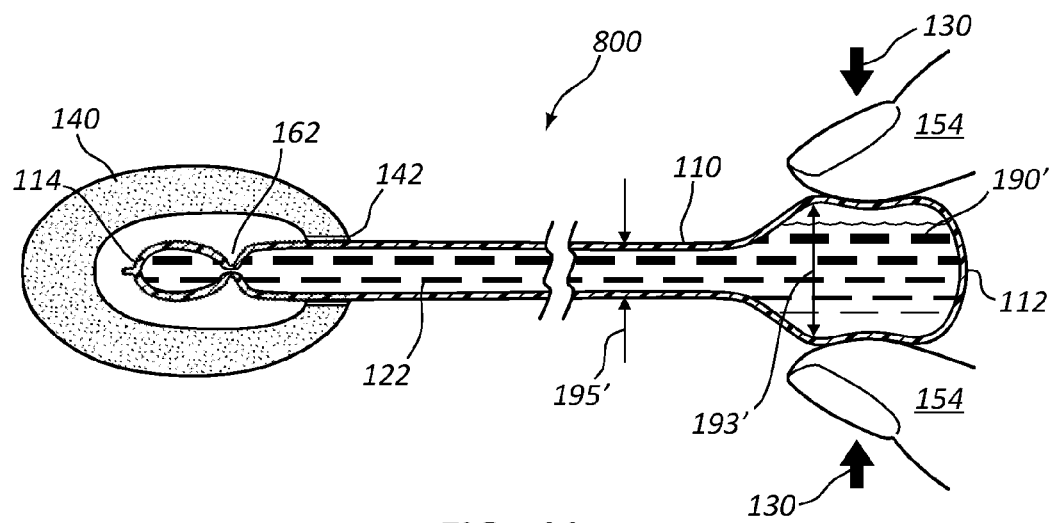
FIG. 11 is a side elevation view in cross section of an antiseptic dispensing applicator having a proximal fluid reservoir in accordance with another representative embodiment of the present invention.

With reference now to FIG. 11, another embodiment of an antiseptic dispensing applicator device 800 comprising a proximal squeeze chamber 190' is illustrated. As shown, device 800 includes various previously discussed elements, including defeatable barrier 162. In some embodiments, device 800 further includes a proximal squeeze chamber 190' located conterminally with proximal end 112 of body 110. User 154 activates device 800 by manually compressing proximal squeeze chamber 190' to thereby apply lateral forces in the direction 130 in order to increase internal hydraulic pressure and thereby defeat defeatable barrier 162 and release antiseptic solution 122 from tube body 110. In such embodiments, proximal squeeze chamber 190' comprises a semi-flexible tubing material capable of being compressed or squeezed by user 154. Following activation, antiseptic solution 122 is released from body 110 in order to saturate or moisten applicator pad 140 for disinfectant use. User 154 may continue to apply lateral forces as necessary to displace additional antiseptic solution 122 from body 110 into applicator pad 140.

In some embodiments, proximal squeeze chamber 190' is enlarged relative to body 110 such that proximal squeeze chamber 190' has a larger diameter 193' than the diameter 195' of body 110. In such configurations, proximal squeeze chamber 190' contains a large quantity of antiseptic solution 122 and enables user generation of internal pressure sufficient to defeat defeatable barrier 162. In some embodiments, body 110 is formed by a two-step process. In some embodiments, body 110 having a diameter 195' is extruded. Then, according to various embodiments, body 110 is cut to length and subjected to a blow molding process to form diameter 193' of proximal squeeze chamber 190'.

Figure 12:
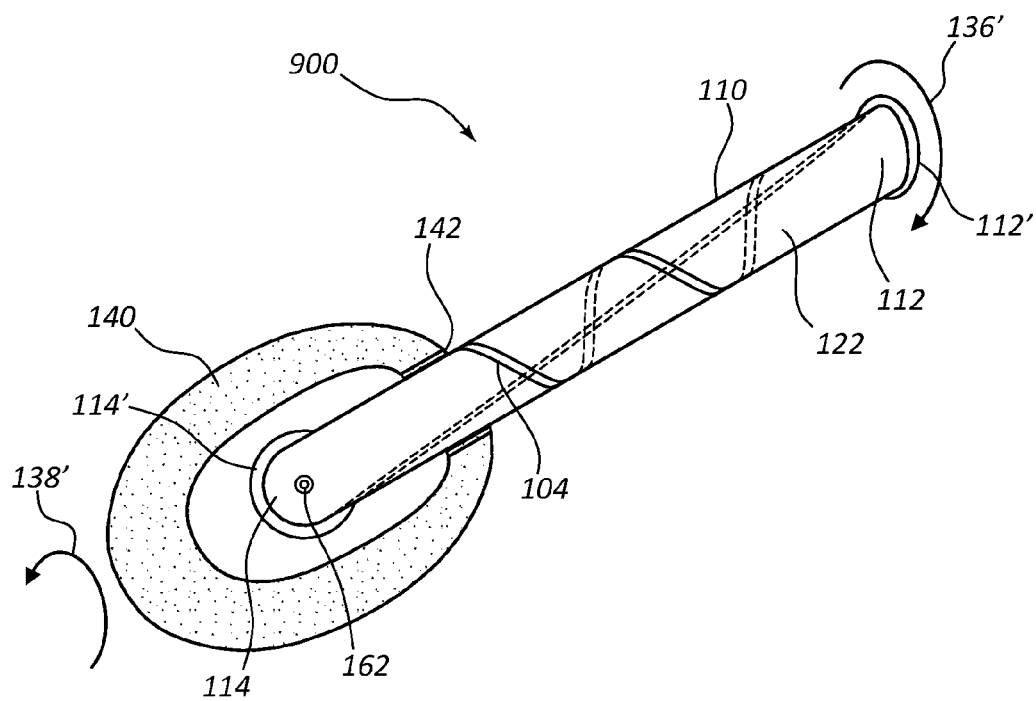
FIG. 12 is a side elevation view in cross section of an antiseptic dispensing applicator device having a twisting configuration in accordance with another representative embodiment of the present invention.

FIG. 12 illustrates another embodiment of an antiseptic dispensing applicator device 900 comprising a twisting configuration. As shown in FIG. 12, according to some embodiments, device 900 includes, among other things, body 110, distal end 112, proximal end 114, antiseptic fluid 122, defeatable barrier 162, and applicator pad 140. Some embodiments of device 900 further include complimentary vertically sealed ends 112' and 114'. According to some embodiments, ends 112' and 114' are orthogonal relative to each other, i.e., ends 112' and 114' are 90 degrees (90°) relative to each other. In still other embodiments, device 900 further includes one or more pre-formed twisting grooves or patterns 104 extending axially along the surface length of body 110 as illustrated. In such embodiments, body 110 comprises a tubing material capable of being twisted by a user without rupturing or failing along twisting grooves 104. In some embodiments, for example, low-density polyethylene (LDPE) is a suitable material for body 110 of device 900. Pre-formed twisting grooves 104 can be formed in body 110 via laser cutting, laser drilling, ultrasonic cutting using a heated blade or pin, or otherwise formed during the manufacturing process.

A user activates device 900 by manually applying opposing torsional forces 136' and 138' to tube body 110. As opposing torsional forces 136' and 138' are applied, twisting grooves 104 and complimentary orthogonal sealed ends 112' and 114' enable body 110 to be twisted thereby axially compressing body 110 and increasing the internal hydraulic pressure thereof. Once the internal hydraulic pressure is sufficiently large, defeatable barrier 162 is defeated and the antiseptic fluid is allowed to flow into applicator pad 140. Following activation, or once defeatable barrier 162 is defeated, antiseptic solution 122 is released from body 110. According to some embodiments, an ergonomic handle or grip is bonded or formed at distal end 112 of device 900 to facilitate the application of manual torsional force to device 900. As elsewhere, in some embodiments, device 900 is capable of being activated while contained within the manufacturer packaging such that the sterility of device 900 is not compromised prior to use.

Referring now to FIGS. 13A-13D, various alternative embodiments of an antiseptic dispensing applicator device employing a body having a defeatable barrier are shown. For example, some embodiments of a device consistent with the present invention include one or more defeatable barrier(s) 162 located at tip 116' of distal end 114. In some embodiments, defeatable barriers 162 comprise the weakest point within body 110 such that, upon a sufficient increase in internal hydraulic pressure within body 110, defeatable barriers 162 will be defeated in a predictable manner. According to some embodiments, defeatable barriers 162 are created by material softening and thinning using heated elements, such as elements 102 (FIG. 9), for soft or semi-flexible plastics. In other embodiments, defeatable barriers 162 are created by cutting or laser drilling for semi-rigid or rigid plastics. In various embodiments, one or more defeatable barrier(s) 162 may be located at any suitable locality on distal end 114 of body 110 so long as defeatable barrier(s) 162 is/are located within the region of body 110 enclosed by applicator pad 140. For example, FIG. 13A depicts a defeatable protruding point at the distal extremity of body 110, FIG. 13B depicts a defeatable notch cut in the lip of distal end 114, FIGS. 13C and 13E illustrate alternative defeatable protruding points at the distal end of body 110, and FIGS. 13D and 13F show additional alternative defeatable notches formed in the lip of distal end 114.

Figure 14:
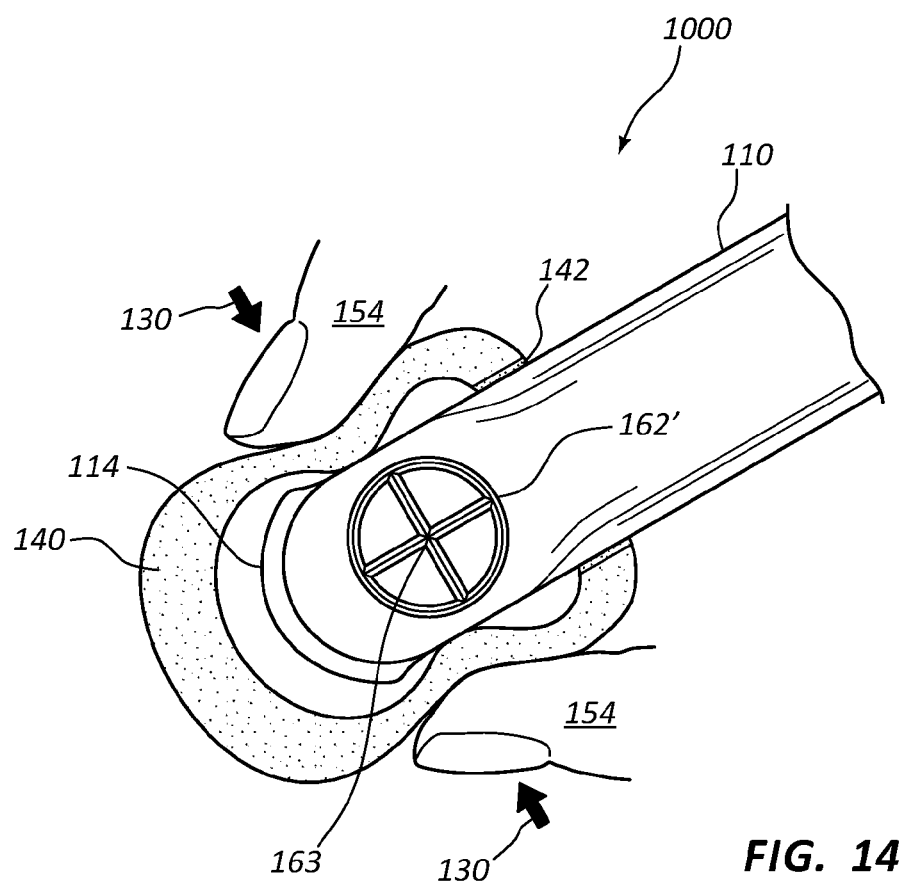
FIG. 14 is a perspective view in cross section of an antiseptic dispensing applicator device having a disk-shaped, weakly sealed tube portion in accordance with another representative embodiment of the present invention.
Figure 14A:
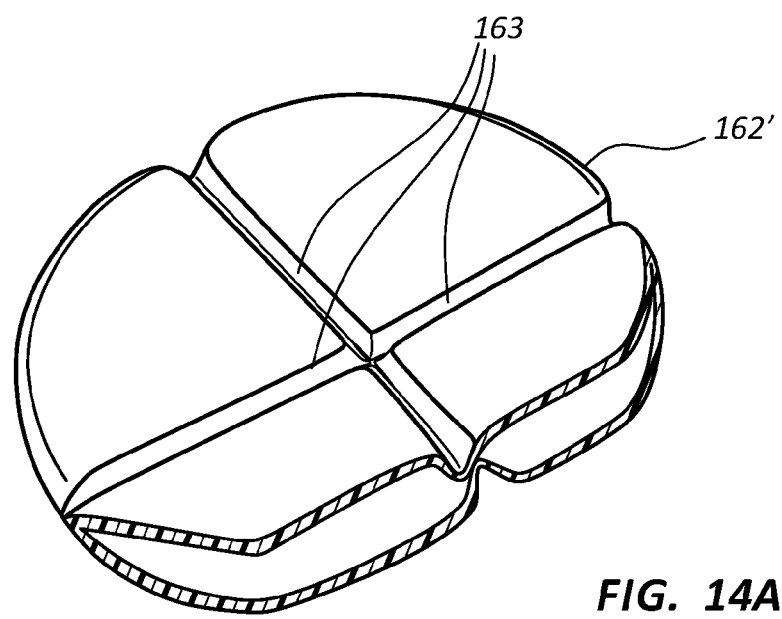
FIG. 14A is an enlarged cross-sectioned view of the weakly sealed tube portion of the antiseptic applicator device of FIG. 14 in accordance with a representative embodiment of the present invention.

With combined reference to FIGS. 14 and 14A, an antiseptic dispensing applicator device 1000 having one or more defeatable barrier(s) 162' in accordance with various representative embodiments is shown. Turning first to FIG. 14, device 1000 includes defeatable barrier 162', which defines a weak or defeatable area. In some embodiments, defeatable barrier 162' is similar to defeatable barriers 162 discuss previously. In other embodiments, defeatable barrier 162' comprises a one sided membrane. In still other embodiments, as illustrated in FIG. 14A, defeatable barrier 162' comprises a two sided membrane. As with other embodiments discussed previously, defeatable barrier 162' defines a weakest point that bursts open when the internal hydraulic pressure of tube body 110 exceeds the barrier strength. According to some embodiments, defeatable barrier 162' is created by material softening and thinning using heated pins for soft or semi-flexible plastics. In other embodiments, defeatable barrier 162' is created by cutting or laser drilling for semi-rigid or rigid plastics. Following activation, antiseptic solution 122 is released from tube body 110 to saturate or moisten applicator pad 140 for disinfectant use.

According to some embodiments, as illustrated in FIGS. 14 and 14A, defeatable barrier 162' comprises a web pattern 163 having a general disk shape with a uniform depression on one side or two sides of the disk. In such embodiments, the thickness of defeatable barrier 162' is lesser at the depression. In this way, when the internal hydraulic pressure of body 110 is sufficiently increased via any of the methods disclosed and discussed herein, the web pattern 163 breaks along the depressions forming a gate vale acting as flow control valve. User 154 is capable of controlling the amount of the antimicrobial solution 122 which passes through the flow control valve defined by web pattern 163 by virtue of controlling the external forces applied to body 110. In such embodiments, web pattern 163 is easily broken by the application of user generated lateral forces in the direction 130, which forces squeeze or compress tube body 110 to thereby increase the internal hydraulic pressure therein and separating or tearing the disk membrane at a predetermine pressure level. User 154 may continue to apply lateral force to displace additional antiseptic solution 122 from body 110 into applicator pad 140.

By way of additional explanation, and with continued reference to FIGS. 14 and 14A, in some embodiments, the scoring associated with defeatable barrier 162' comprises a webbed pattern 163 featuring a plurality of scorings having varying dimensions and yield strengths. For example, in some embodiments, portions of defeatable barrier 162' are scored at varying depths or graduated depths to provide various yield strengths across the defeatable barrier 162'. Thus, when compressed with a lateral force, defeatable barrier 162' breaks along some of the scored surface 163 to form a gate valve as indicated above. Since only some of the scored surfaces 163 are defeated, the partially defeated defeatable barrier 162' controls flow of the antiseptic agent 122 through the defeatable barrier 162'. However, upon the application of additional lateral force to the reservoir defined by body 110, additional portions of the scored surfaces 163 are defeated thereby increasing the amount of antiseptic agent 122 permitted to flow through the defeatable barrier 162'.

As mentioned above, in some embodiments, defeatable barrier 162' is disk-shaped having a uniform depression or scoring 163 that is broken or defeated by applying lateral force thereto. In some embodiments, scoring 163 is broken by applying an external force to the applicator pad 140, whereby the force is transferred to defeatable barrier 162', such as striking or pressing applicator pad 140 against an object proximate defeatable barrier 162'. In other embodiments, scoring 163 is broken from internal pressure resulting from compressing or squeezing the fluid reservoir defined by body 110 to increase the pressure within the reservoir beyond the strength of the scored surface 163. Once defeated, antiseptic solution 122 within the reservoir flows through defeatable barrier 162' and is absorbed by applicator pad 140. The thickness of defeatable barrier 162' and the depth of scoring 163 may be varied dependent upon the calculated force desired to defeat defeatable barrier 162'.

Figure 15:
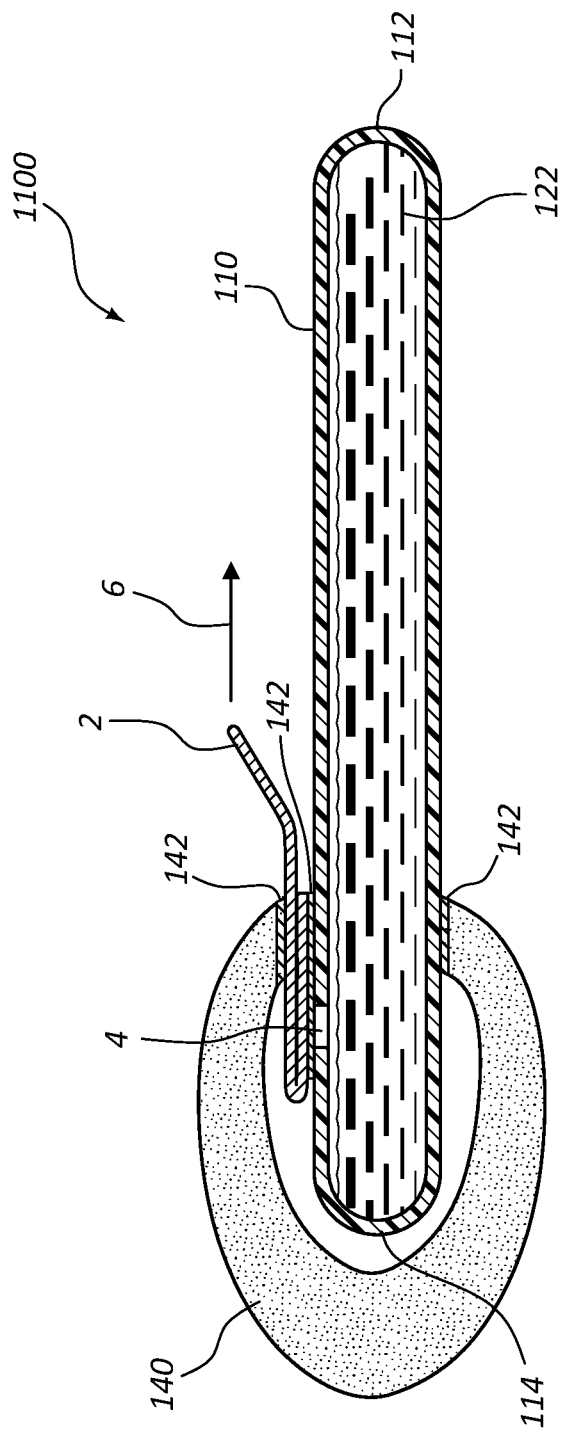
FIG. 15 is a side elevation view in cross section of an antiseptic dispensing applicator device having a removable pull-tab seal in accordance with another representative embodiment of the present invention.

With reference now to FIGS. 15, 16 and 16A, additional alternative embodiments of an antiseptic dispensing applicator device employing a removable pull-tab seal are shown. Turning first to FIG. 15, a side elevation view in cross section of an antiseptic dispensing applicator device 1100 having pull-tab 2 is shown. FIG. 15 depicts device 1100 prior to activation. As illustrated, according to various embodiments, body 110 of device 1100 includes one or more pre-formed openings 4 disposed therein. Absent pull-tab 2, openings 4 comprise a fluid communication pathway between applicator pad 140 and the fluid contents 122 of body 110. Openings 4 may be located at any suitable point on distal end 114 of body 110 so long as openings 4 are located within the region of body 110 enclosed by applicator pad 140. Upon removal of pull-tab 2, antiseptic fluid 122 is released from tube body 110 in order to saturate or moisten applicator pad 140 for disinfectant use. Openings 4 may be formed in any suitable shape, such as, but not limited to, circular, elliptical, rectangular, oval, crescent, triangular, square and so forth. Similarly, openings 4 may be formed in any suitable patterns, such as a series of smaller holes or perforations forming a desired pattern.

As illustrated in FIG. 15, prior to activation, pull-tab 2 is attached or affixed to the exterior of body 110 so as to sealingly cover opening(s) 4. In this way, prior to the removal of pull-tab 2, pull-tab 2 interposes a temporary fluid seal or defeatable barrier between the fluid contents 122 of the lumen defined by body 110 and applicator pad 140. According to various embodiments, pull-tab 2 is attached to the exterior of body 110 via removable adhesive that is compatible with the antiseptic agent 122. In some embodiments, as illustrated in FIG. 15, pull-tab 2 extends from the distal end thereof, where it is sealingly engaged with body 110 adjacent opening(s) 4, proximally through applicator pad 140 and to a sufficient length so as to render pull-tab 2 easily graspable. As illustrated in FIG. 15, in such embodiments, device 1100 is activated by the application of force in the direction 6. In other embodiments, as illustrated in FIG. 16, pull-tab 2 extends from the proximal end thereof, where it is sealingly engaged with body 110 adjacent opening(s) 4, distally through applicator pad 140 and to a sufficient length so as to render pull-tab 2 easily graspable. As illustrated in FIG. 16, in some embodiments, device 1100 is activated by the application of force in the direction 6'. Pull-tab 2 may have any suitable shape or dimensions so as to be capable of sealingly covering opening(s) 4 and having a suitable gripping length and surface.

As mentioned above, in some embodiments, device 1100 is activated as the user grasps the proximal tail or end of pull-tab 2 and applies removing force thereto. In this way, the bond strength of the adhesive between pull-tab 2 and the exterior of body 110 is overcome by the application of force in the direction 6 and the user continues to apply removing force until pull-tab 2 is fully removed proximally and discarded. In other embodiments, as shown in FIG. 16, device 1100 is activated as the user grasps the distal tail or end of pull-tab 2 and applies removing force in the direction 6' until pull-tab 2 is fully removed distally and discarded. FIG. 16A depicts device 1100 following activation via removal of pull-tab 2.

In some embodiments, pull-tab 2 extends through an opening or cavity 8 formed through applicator pad 140. The opening or cavity 8 can be formed on the distal end of applicator pad 140, as illustrated in FIGS. 16 and 16A. In alternative embodiments, opening or cavity 8 can be formed on the proximal end of applicator pad 140, as illustrated in FIG. 15. In still other embodiments, applicator pad 140 comprises a two-piece applicator pad having a gap between the two halves thereof through which pull-tab 2 extends.

As with previous embodiments discussed and disclosed herein, device 1100 can be squeezed or compressed following removal of pull-tab 2 such that the fluid contents 122 thereof are encouraged to flow through opening 4 and into applicator pad 140 for use. Other features discussed in connection with the embodiments disclosed herein can be employed in concert with opening(s) 4 and/or pull-tab 2.

Turning now to FIGS. 17A through 17D, additional alternative embodiments of an antiseptic dispensing applicator device employing a low peel strength seal are shown. The aforementioned figures depict side elevation views in cross section of various antiseptic dispensing applicator devices 1200 having low peel strength seal 9 according to various embodiments. As illustrated, according to some embodiments, body 110 of device 1200 includes one or more pre-formed openings 4 disposed therein. In such embodiments, seal 9 operates as a defeatable barrier.

Prior to activation, one end 9A of low peel strength seal 9 is attached or affixed to the interior of applicator head or pad 140 and the other end 9B of seal 9 is attached or affixed to the exterior of body 110 so as to sealingly cover opening (s) 4. In this way, prior to the removal thereof, seal 9 interposes a temporary fluid seal or defeatable barrier between the fluid contents 122 of the lumen defined by body 110 and applicator pad 140. According to various embodiments, seal 9 is attached to the exterior of body 110 at 9B using a relatively low bond strength, removable adhesive that is compatible with the antiseptic agent 122. End 9A, on the other hand, is attached to the interior of applicator pad 140 using a relatively high bond strength and/or generally permanent adhesive that is also compatible with antiseptic agent 122. The adhesive employed at 9A has a bond strength that exceeds the adhesive employed at 9B. As depicted in FIGS. 17A through 17D, seal 9 is attached in a folded configuration with a leading or peeling end 9C configured to facilitate activation of device 1200.

Figure 17A:
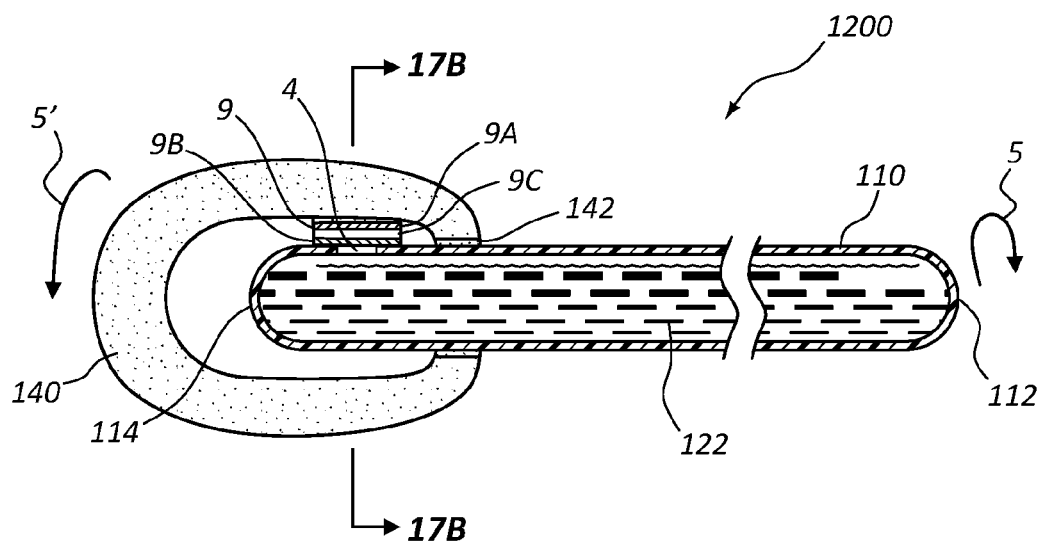
FIG. 17A is a side elevation view in cross section of an antiseptic dispensing applicator device having a low peel strength seal in accordance with another representative embodiment of the present invention.
Figure 17B:
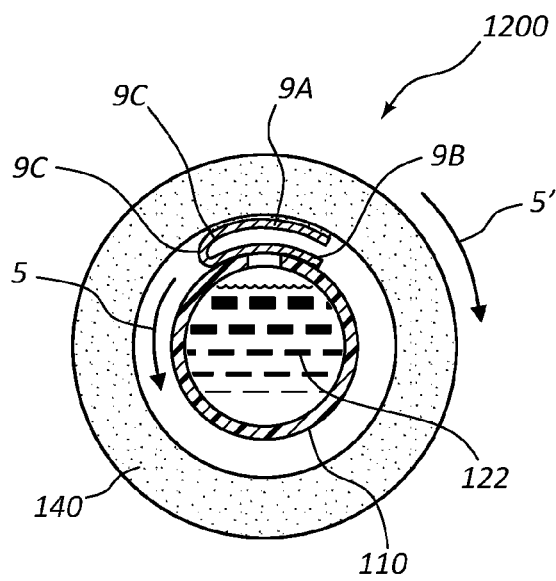
FIG. 17B is a longitudinal cross-sectional view of the device of FIG. 17 in the direction A-A in accordance with another representative embodiment of the present invention.

With reference to FIGS. 17A and 17B, seal 9 is attached between applicator pad 140 and the exterior of body 110 about opening(s) 4 as described above. As depicted, in some embodiments, seal 9 is oriented such that the leading or pealing edge 9C is generally parallel with the longitudinal axis of body 110. In this way, according to some embodiments, device 1200 is activated by opposing rotational forces 5 and 5'. As shown in FIGS. 17A and 17B, device 1200 is activated as the user grasps applicator pad 140 with one hand and body 110 with the other hand and applies opposing rotational forced 5 and 5' such that the relatively weak bond strength adhesive at 9B is overcome as seal 9 remains attached to applicator pad 140 at 9A and, therefore, rotationally moves with applicator pad 140 until seal 9 is fully or partially removed at 9B. In some embodiments, device 1200 is capable of being grasped and activated as described while still fully or partially in its original packaging.

Figure 17C:
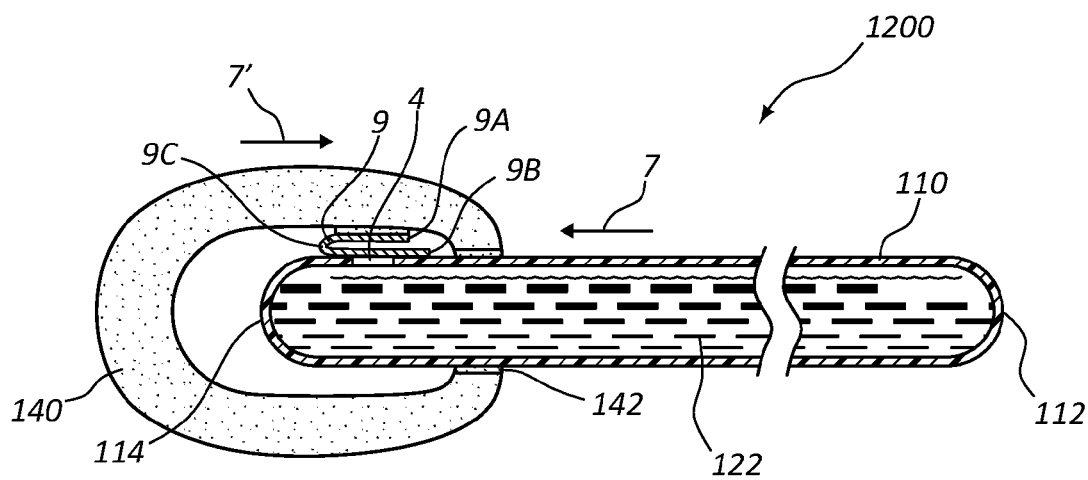
FIG. 17C is a side elevation view in cross section of an antiseptic dispensing applicator device having an alternative low peel strength seal in accordance with another representative embodiment of the present invention.
Figure 17D:
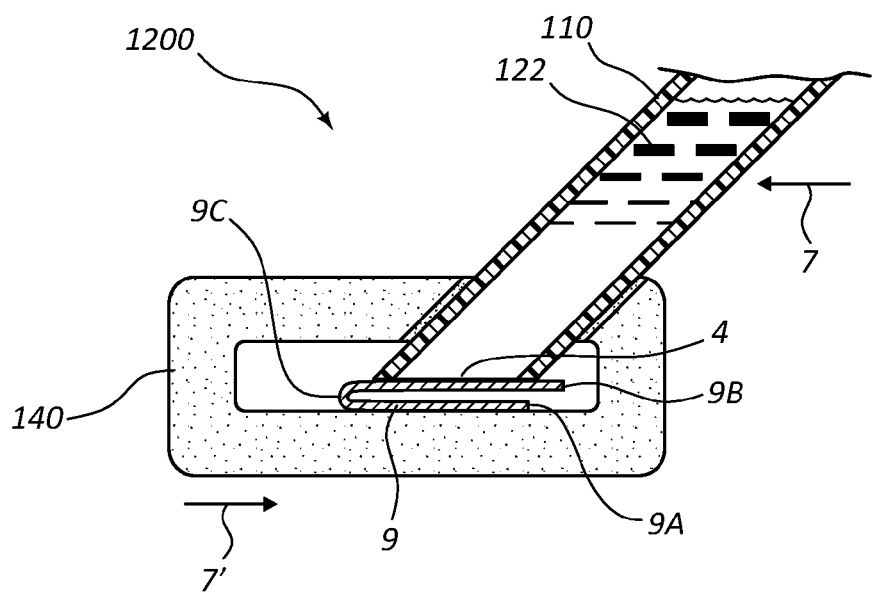
FIG. 17D is a side elevation view in cross section of an antiseptic dispensing applicator device having yet another alternative low peel strength seal in accordance with another representative embodiment of the present invention.

In other embodiments, as depicted in FIGS. 17C and 17D, seal 9 is oriented such that the leading or pealing edge 9C is generally transverse or perpendicular relative to the longitudinal axis of body 110. In this way, according to some embodiments, device 1200 is activated by opposing longitudinal forces 7 and 7'. In such embodiments, seal 9 is induced to fail or release at 9B due to the application of opposing longitudinal forces 7 and 7' as seal 9 moves longitudinally with applicator pad 140 until seal 9 is fully or partially removed at 9B. In some embodiments, device 1200 is activated as the distal end of applicator pad 140 is held against a stationary surface and a user applies longitudinal force 7, which force is equally and oppositely opposed by the stationary surface supplying opposing longitudinal force 7'. In this way, device 1200 can be activated using a one-handed operation or technique.

As with previous embodiments discussed and disclosed herein, device 1200 can be squeezed or compressed following removal of seal 9 at 9B such that the fluid contents 122 thereof are encouraged to flow through opening 4 and into applicator pad 140 for use. Other features discussed in connection with the embodiments disclosed herein can be employed in concert with seal 9.

The present invention may be embodied in other specific forms without departing from its structures, methods, or other essential characteristics as broadly described herein. For example, in some embodiments, a one-way valve (not shown) may be incorporated into the distal end 114 of body 110 of devices 100-1200. In such embodiments, the one-way valve is interposed between the contents of the fluid reservoir defined by body 110 and applicator pad 140. Such a one-way valve generally comprises a flexible or semi-flexible polymer material that is secured within the distal end 114 of body 110 proximate applicator pad 140. In some embodiments, the one-way valve includes a duckbill or an umbrella valve. In other embodiments, the one-way valve includes a slit that is biased to a closed position so as to prevent fluid communication between the fluid reservoir defined by body 110 and applicator pad 140 prior to activation. However, as discussed and disclosed herein, when a pressure within body 110 exceeds the threshold pressure of the one-way valve, the one-way valve is defeated such that the slit opens to provide fluid communication between the fluid reservoir defined by body 110 and applicator pad 140.

For example, as discussed at length previously, in some embodiments the body portion 110 of devices 100-1200 comprises a semi-flexible tubing material capable of being compressed or squeezed by the user. Thus, as the user compresses the body portion 110, the pressure within the inner lumen thereof increases to exceed the threshold pressure of the one-way valve. When this occurs, the one-way valve is defeated and the antiseptic agent 122 is permitted to bypass the one-way valve, via the slit, and flow into applicator pad 140. When the pressure subsides, the valve closes to prevent further flow of antiseptic fluid 122 into applicator pad 140. In some embodiments, the one-way valve is replaced with a mechanical valve (not shown) that the user directly manipulates, such as a flapper or sliding valve. In other embodiments, the defeatable barrier 162 and/or 162' discussed herein is replaced with a small hole that would allow antiseptic agent 122 to flow from the inner lumen defined by body 110 into applicator pad 140 when body portion 110 is compressed. However, fluid would not be permitted to flow without compression due to the inner lumen being unvented and due to the surface tension of the antiseptic agent 122.

While applying positive pressure to the body portion 110 of the devices 100-1200 is one method to defeat the one-way valve as well as defeatable barrier 162 and/or 162', one of skill in the art will appreciate that other methods may be used to equally defeat the one-way valve as well as the weakened membrane. For example, in some embodiments, the fluid chamber defined by body 110 is modified to include a vacuum source whereby the pressure within the fluid chamber defined by body 110 is decreased below the threshold pressure of the one-way valve. In other embodiments, body 110 itself comprises a syringe (not shown) containing an antiseptic agent 122. As the syringe is compressed, antiseptic agent 122 is injected directly into applicator pad 140 and the user maintains precise control over the amount of antiseptic agent supplied. In still other embodiments, a syringe (not shown) is attached to body 110 in order to manually depress the syringe plunger and thereby controllably increase the pressure within body 110. When the pressure within the inner lumen defined by body 110 exceeds the threshold pressure of the one-way valve and/or defeatable barrier 162 and/or 162', the valve and/or membrane is defeated and the antiseptic agent 122 flows into applicator pad 140.

In yet additional embodiments, body 110 includes two or more internal lumens separated by internal axial membranes. In such embodiments, the multiple lumens of body 110 are configured to contain the same or different solutions. Different solutions may be useful for procedures requiring a two-step preparation. For example, in some embodiments, the first lumen contains a detergent solution while the second lumen contains a disinfectant solution. According to some embodiments, the lumens of body 110 release their contents simultaneously via a single action. In other embodiments, the lumens of body 110 release their contents in stages requiring a unique action associated with each individual lumen.

In various embodiments, body 110 is configured to ergonomically enhance the user's grip. For example, in some embodiments, body 110 is sized and shaped to as to provide an adequate gripping surface and length. In other embodiments, body 110 is formed with ergonomic shapes complimentary to the user's grip. In still other embodiments, body 110 includes an external treatment, texture, or contours so as to increase the coefficient of friction between body 110 and a user's hand to thereby facilitate a user's grip. Finally, according to various embodiments, body 110 is sized and shaped to enhance manual dexterity and the functionality of devices 100-1200 suitable to the procedure being performed. For example, the size of body 110 may be increased for procedures requiring a large volume of antiseptic agent 122. Alternatively, the size of body 110 may be decreased to ensure adequate control over the device by a desired grip.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

What is claimed is:

1. An applicator device, comprising:
    a body having a lumen for receiving an antiseptic agent, the lumen defining a reservoir containing the antiseptic agent, wherein the lumen is sealed at a distal extremity and a proximal extremity thereof following receipt of the antiseptic agent;
    a pad coupled to a distal end of the body;
    a defeatable barrier interposedly positioned between the reservoir and the pad, wherein upon defeating the barrier, the reservoir and the pad are in fluid communication, wherein the defeatable barrier is enclosed within the pad; and
    a pinching actuator coupled adjacent the distal end of the body between the body and the pad, wherein the pinching actuator is configured to defeat the defeatable barrier upon actuation.

2. The device of claim 1, wherein the distal end of the body is cone-shaped and wherein a tip of the distal end includes a weakened formation thereon.

3. The device of claim 1, further comprising an air vent located within the body, wherein the body comprises a semi-flexible material and upon compressing the body the barrier is defeated.

4. The device of claim 3, wherein the defeatable barrier comprises a membrane having a first thickness and a second thickness, the second thickness being configured to break in response to increased pressure within the reservoir when the body is compressed.

5. The device of claim 1, wherein the body comprises a proximal portion and a distal portion, the proximal portion having a diameter which is smaller than the diameter of the distal portion.

6. A method for manufacturing an applicator device, comprising:
providing a body having a lumen for receiving an antiseptic agent, the lumen defining a reservoir for containing the antiseptic agent;
filling the reservoir with the antiseptic agent;
sealing a distal extremity and a proximal extremity of the reservoir after the reservoir is filled with antiseptic agent;
coupling a pad to a distal end of the body;
enclosing a defeatable barrier within the pad, wherein upon defeating the barrier, the reservoir and the pad are brought into fluid communication with each other; and
coupling a pinching actuator adjacent the distal end of the body between the body and the pad, wherein the pinching actuator is configured to defeat the defeatable barrier upon actuation.

7. The method of claim 6, wherein the body further comprises an air vent located therein, and wherein the body comprises a semi-flexible material and upon compressing the body the barrier is defeated.

8. The method of claim 6, further comprising forming the defeatable barrier in a wall of the body by one of laser cutting, laser drilling, ultrasonic cutting, and using a heated element.

* * * * *